(12) United States Patent
Hirota et al.

(10) Patent No.: US 11,340,215 B2
(45) Date of Patent: May 24, 2022

(54) SCREENING METHOD OF ANTICANCER AGENT FOCUSED ON FUNCTION OF HP1 AND EVALUATION SYSTEM

(71) Applicant: JAPANESE FOUNDATION FOR CANCER RESEARCH, Tokyo (JP)

(72) Inventors: Toru Hirota, Tokyo (JP); Yusuke Abe, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 111 days.

(21) Appl. No.: 16/079,895

(22) PCT Filed: Feb. 27, 2017

(86) PCT No.: PCT/JP2017/007444
§ 371 (c)(1),
(2) Date: Aug. 24, 2018

(87) PCT Pub. No.: WO2017/146253
PCT Pub. Date: Aug. 31, 2017

(65) Prior Publication Data
US 2019/0094207 A1  Mar. 28, 2019

(30) Foreign Application Priority Data
Feb. 26, 2016 (JP) .............................. JP2016-035505

(51) Int. Cl.
| | |
|---|---|
| *G01N 33/50* | (2006.01) |
| *C07K 16/18* | (2006.01) |
| *G01N 33/574* | (2006.01) |
| *G01N 33/68* | (2006.01) |
| *C12N 15/113* | (2010.01) |

(52) U.S. Cl.
CPC .......... *G01N 33/5011* (2013.01); *C07K 16/18* (2013.01); *G01N 33/574* (2013.01); *G01N 33/6845* (2013.01); *C07K 2317/30* (2013.01); *C07K 2317/32* (2013.01); *C07K 2317/70* (2013.01); *C12N 15/113* (2013.01); *C12N 2310/14* (2013.01); *G01N 2440/14* (2013.01); *G01N 2500/02* (2013.01)

(58) Field of Classification Search
CPC ............. G01N 33/5011; G01N 33/574; G01N 33/6845; G01N 2500/02; C07K 16/18; C07K 2317/32; C07K 2317/70
See application file for complete search history.

(56) References Cited

U.S. PATENT DOCUMENTS

| | | | |
|---|---|---|---|
| 8,592,581 B2 | 11/2013 | Sheldrake et al. | |
| 9,447,092 B2 | 9/2016 | Blagg et al. | |

FOREIGN PATENT DOCUMENTS

| | | |
|---|---|---|
| JP | 2002-236125 | 8/2002 |
| JP | 2010-523534 | 7/2010 |
| JP | 2015-520222 | 7/2015 |
| WO | 2008/013807 | 1/2008 |
| WO | 2008/063525 | 5/2008 |
| WO | 2014/112144 | 7/2014 |

OTHER PUBLICATIONS

Japanese Office Action dated Apr. 11, 2019, Application No. 2018-501823, English translation included, 6 pages.
"Anti-HP1 alpha (phospho S92) antibody ab50514", [online], 2007; URL:<https://www.abcam.co.jp/hp1-alpha-phospho-s92-antibody-ab50514.pdf>.
Thompson, et al. 2010, NIH Public Access Author Manuscript, "Mechanisms of Chromosomal Instability", Curr. Biol. vol. 20, R285-R295, 23 pages.
Kelly, et al. 2009, NIH Public Access Author Manuscript, "Correcting Aberrant Kinetochore Microtubule Attachments: An Aurora B-centric View", Curr. Opin. Cell Biol. vol. 21, p. 51-58, 13 pages.
Carmena, et al. 2012, NIH Public Access Author Manuscript, "The Chromosomal Passenger Complex (CPC): From Easy Rider to the Godfather of Mitosis", Nat Rev Mol Cell Biol., vol. 13, p. 789-803, 33 pages.
Cimini, et al. 2006, "Aurora Kinase Promotes Turnover of Kinetochore Microtubules to Reduce Chromosome Segregation Errors", Current Biology, vol. 16, p. 1711-1718, 8 pages.
Ainsztein, et al. "INCENP Centromere and Spindle Targeting: Identification of Essential Conserved Motifs and Involvement of Heterochromatin Protein HP1", 1998, The Journal of Cell Biology, vol. 143, p. 1763-1774, 12 pages.
Kang et al. 2011, "Mitotic Centromeric Targeting of HP1 and its Binding to Sgo1 are Dispensable for Sister-Chromatid Cohesion in Human Cells", Mol Biol Cell, vol. 22, p. 1181-1190, 10 pages.
Salimian, et al. "Feedback Control in Sensing Chromosome Biorientation by the Aurora B Kinase", 2011, Curr. Biol., vol. 21, p. 1158-1165, 8 pages.
Deluca, et al. 2011, "Temporal Changes in Hec1 Phosphorylation Control Kinetochore-Microtubule Attachment Stability During Mitosis", J. Cell, Sci. vol. 124, p. 622-634, 13 pages.

(Continued)

*Primary Examiner* — Shafiqul Haq
(74) *Attorney, Agent, or Firm* — Rankin, Hill & Clark LLP

(57) ABSTRACT

The inventors have found that the interaction between HP1 and INCENP can serve as an indicator for chromosome instability and established a method for evaluating chromosome instability of cancer cells. The evaluation system can be used for screening of anticancer agent with a new-concept of targeting chromosome instability of cancer cells. The inventors further prepared an antibody for specifically recognizing phosphorylation of serine at position 92 of HP1α, by which the action of Aurora B can be evaluated. The interaction between HP1 and INCENP can be readily evaluated by the antibody.

3 Claims, 12 Drawing Sheets
Specification includes a Sequence Listing.

(56) References Cited

OTHER PUBLICATIONS

Zaytsev, et al. 2014, "Accurate Phosphoregulation of Kinetochore-Microtubule Affinity Requires Unconstrained Molecular Interactions", J. Cell. Biol. vol. 206, p. 45-59, 15 pages.
Brasher, et al. 2000, "The Structure of Mouse HP1 Suggests a Unique Mode of Single Peptide Recognition by the Shadow Chromo Domain Dimer", The EMBO Journal, vol. 19., No. 7, p. 1587-1597, 11 pages.
Takagaki, et al. "Regulation of M Phase Checkpoint by Aurora B", Journal of Japanese Biochemical Society. 2008, Abstract CD, p. 2T11-4, 2 pages.
Hiragami-Hamada, "N-Terminal Phosphorylation of HP1(alpha) Promotes its Chromatin Binding", Molecular and Cellular Biology, 2011, vol. 31, No. 6, p. 1186-1200, p. 1189 (Mouse HP1 (alpha) Exhibits Two Distinct Types of Phosphorylation), p. 1191 (Determination of the Phosphorylation Sites of Mouse HP1 alpha), Fig. 2, 15 pages.
Abe, "HP1 Ensures Orderly Mitotic Chromsome Partitioning", The Japanese Cancer Association Symposium/Kyodo Riyo-Kyodo Kenkyu Kyoten Symposium Shorokushu, 2015, p. 42, 3 pages.
Chakraborty; et al. "Dynamic Phosphorylation of Hp1(alpha) Regulates Mitotic Progression in Human Cells", Nature Communications, 2014, vol. 5, p. 4445/1-4445/14, p. 4, right col. to p. 5, left col. Fig 3, 14 pages.
Grzenda, et al. "Functional Impact of Aurora A-Mediated Phosphorylation of Hp1y at Serine 83 During Cell Cycle Progression", Epigenetics Chromatin, Jul. 2013, vol. 6, No. July, p. 6-21, Abstract, 15 pages.
International Search Report, Application No. PCT/JP2017/007444, dated May 23, 2017, 5 pages.
International Preliminary Report on Patentability, Application No. PCT/JP2017/007444, dated Aug. 28, 2018, 8 pages.

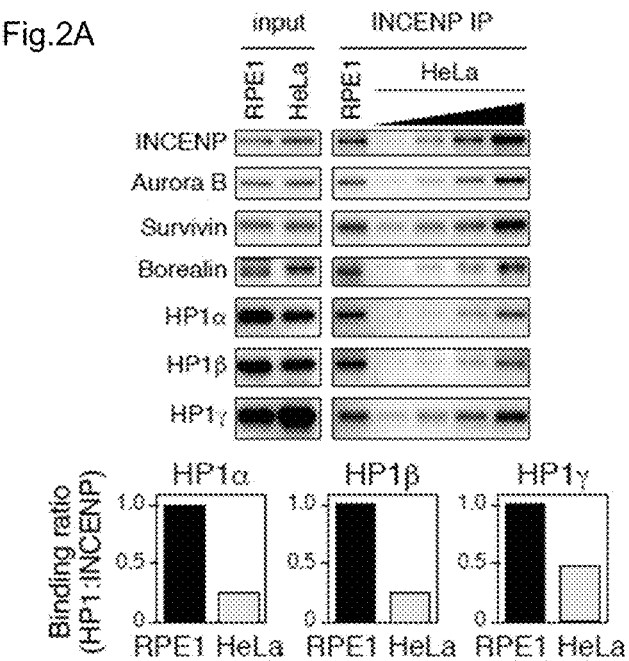
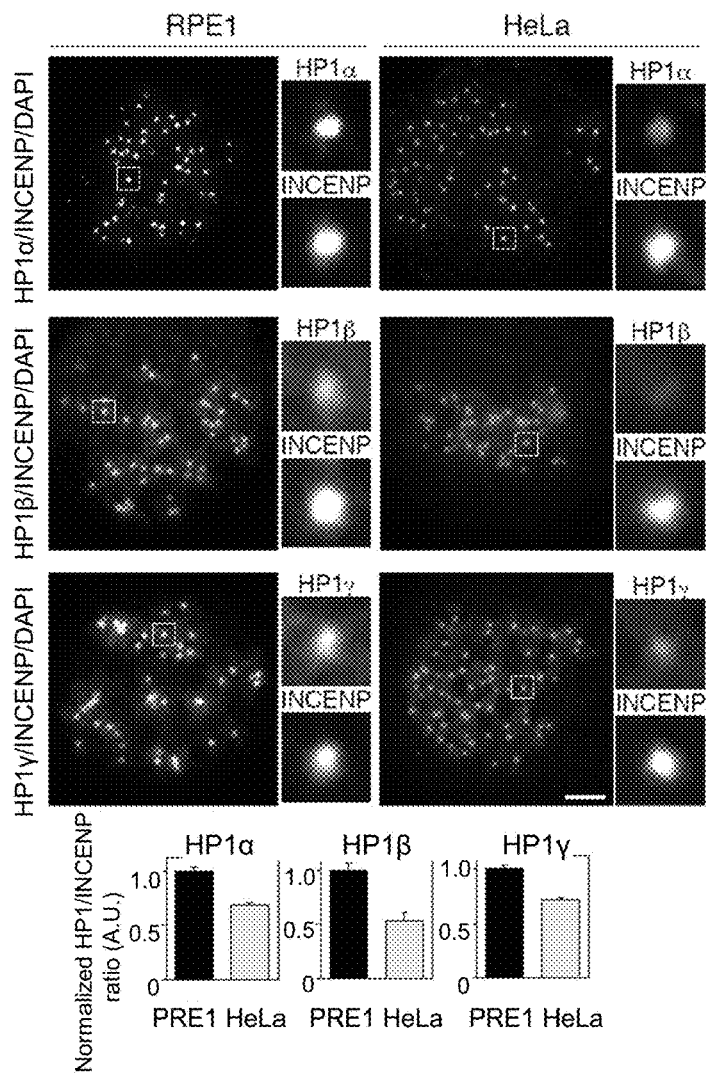

Fig.5E
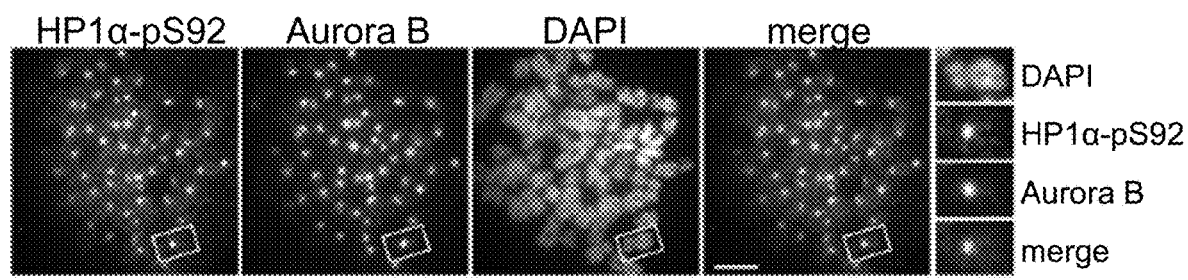
Fig.5F
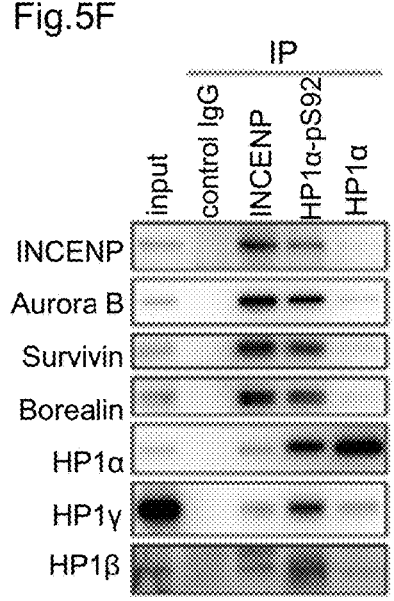
Fig.5G
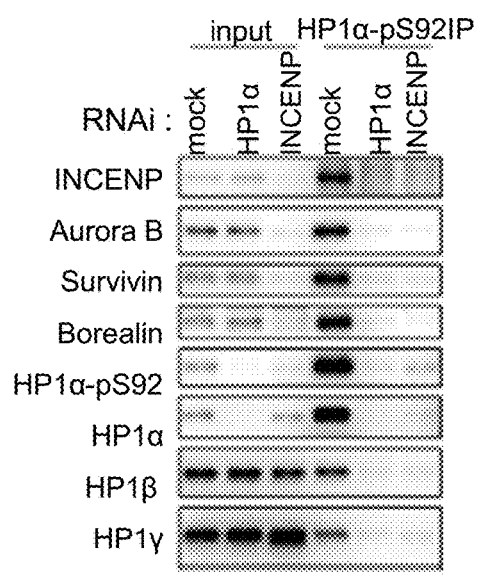
Fig.5H
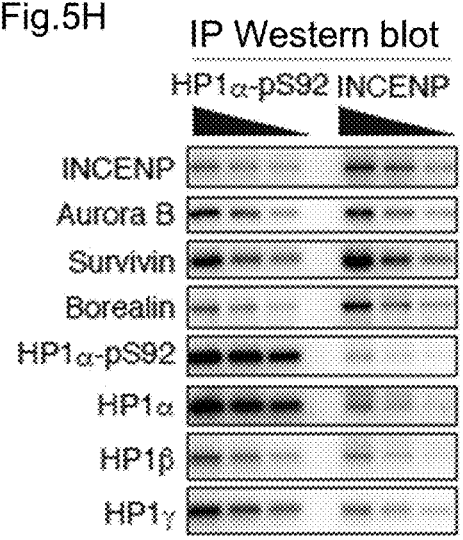
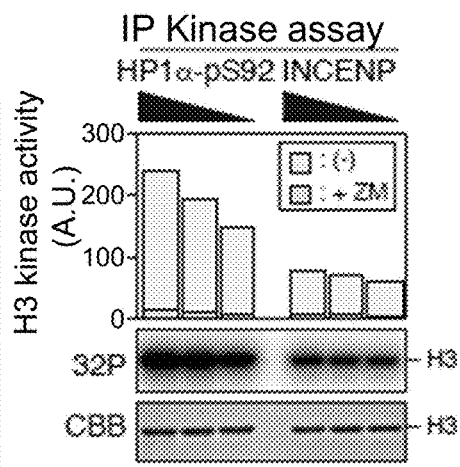

Fig.6A 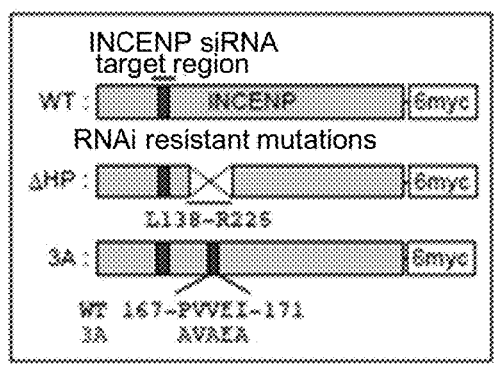 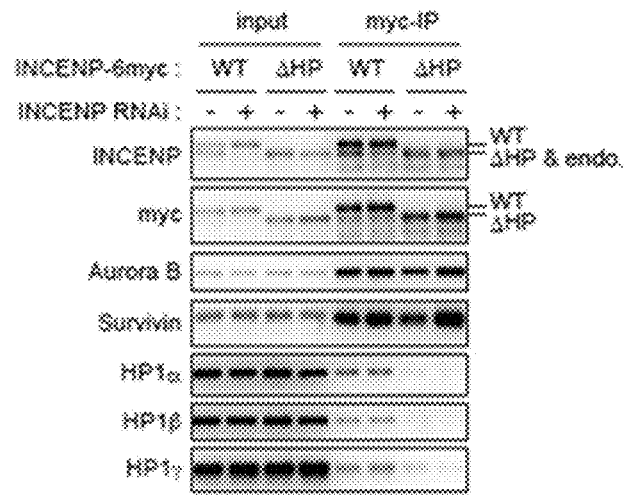

SEQUENCE LISTING

```
<160> NUMBER OF SEQ ID NOS: 10

<210> SEQ ID NO 1
<211> LENGTH: 20
<212> TYPE: PRT
```

```
<213> ORGANISM: Artificial Sequence
<220> FEATURE:
<223> OTHER INFORMATION: INCENP epitope

<400> SEQUENCE: 1

Cys Asp Leu Glu Asp Ile Phe Lys Lys Ser Lys Pro Arg Tyr His Lys
1               5                   10                  15

Arg Thr Ser Ser
            20

<210> SEQ ID NO 2
<211> LENGTH: 11
<212> TYPE: PRT
<213> ORGANISM: Artificial Sequence
<220> FEATURE:
<223> OTHER INFORMATION: HP1a epitope
<220> FEATURE:
<221> NAME/KEY: HP1
<222> LOCATION: (6)..(6)
<223> OTHER INFORMATION: PHOSPHORYLATION C+NKRK(pS)NFSNS

<400> SEQUENCE: 2

Cys Asn Lys Arg Lys Ser Asn Phe Ser Asn Ser
1               5                   10

<210> SEQ ID NO 3
<211> LENGTH: 25
<212> TYPE: RNA
<213> ORGANISM: Artificial Sequence
<220> FEATURE:
<223> OTHER INFORMATION: INCENP siRNA target

<400> SEQUENCE: 3
caguguagag aagcuggcua cagug                                    25

<210> SEQ ID NO 4
<211> LENGTH: 25
<212> TYPE: RNA
<213> ORGANISM: Artificial Sequence
<220> FEATURE:
<223> OTHER INFORMATION: HP1a siRNA target, 5'UTR

<400> SEQUENCE: 4
ccuuagucuu ucagguggaa cggug                                    25

<210> SEQ ID NO 5
<211> LENGTH: 25
<212> TYPE: RNA
<213> ORGANISM: Artificial Sequence
<220> FEATURE:
<223> OTHER INFORMATION: HP1a siRNA target, ORF

<400> SEQUENCE: 5
uaacaagagg aaauccaauu ucuca                                    25

<210> SEQ ID NO 6
<211> LENGTH: 25
<212> TYPE: RNA
<213> ORGANISM: Artificial Sequence
<220> FEATURE:
<223> OTHER INFORMATION: HP1b siRNA target

<400> SEQUENCE: 6
ggauaagugu uucaaggcaa ccuuu                                    25

<210> SEQ ID NO 7
```

```
<211> LENGTH: 25
<212> TYPE: RNA
<213> ORGANISM: Artificial Sequence
<220> FEATURE:
<223> OTHER INFORMATION: HP1r siRNA target

<400> SEQUENCE: 7
ucuuaacucu cagaaagcug gcaaa                                               25

<210> SEQ ID NO 8
<211> LENGTH: 150
<212> TYPE: PRT
<213> ORGANISM: Homo sapiens

<400> SEQUENCE: 8

Leu Arg Arg Val Thr Arg Ala Ala Ala Ala Ala Ala Ala Ala Thr Met
1               5                   10                  15

Ala Leu Ala Ala Pro Ser Ser Pro Thr Pro Glu Ser Pro Thr Met Leu
                20                  25                  30

Thr Lys Lys Pro Glu Asp Asn His Thr Gln Cys Gln Leu Val Pro Val
            35                  40                  45

Val Glu Ile Gly Ile Ser Glu Arg Gln Asn Ala Glu Gln His Val Thr
50                  55                  60

Gln Leu Met Ser Thr Glu Pro Leu Pro Arg Thr Leu Ser Pro Thr Pro
65                  70                  75                  80

Ala Ser Ala Thr Ala Pro Thr Ser Gln Gly Ile Pro Thr Ser Asp Glu
                85                  90                  95

Glu Ser Thr Pro Lys Lys Ser Lys Ala Arg Ile Leu Glu Ser Ile Thr
            100                 105                 110

Val Ser Ser Leu Met Ala Thr Pro Gln Asp Pro Lys Gly Gln Gly Val
        115                 120                 125

Gly Thr Gly Arg Ser Ala Ser Lys Leu Arg Ile Ala Gln Val Ser Pro
    130                 135                 140

Gly Pro Arg Asp Ser Pro
145                 150

<210> SEQ ID NO 9
<211> LENGTH: 150
<212> TYPE: PRT
<213> ORGANISM: Artificial Sequence
<220> FEATURE:
<223> OTHER INFORMATION: HP1 binding site mutant

<400> SEQUENCE: 9

Leu Arg Arg Val Thr Arg Ala Ala Ala Ala Ala Ala Ala Ala Thr Met
1               5                   10                  15

Ala Leu Ala Ala Pro Ser Ser Pro Thr Pro Glu Ser Pro Thr Met Leu
                20                  25                  30

Thr Lys Lys Pro Glu Asp Asn His Thr Gln Cys Gln Leu Val Ala Val
            35                  40                  45

Ala Glu Ala Gly Ile Ser Glu Arg Gln Asn Ala Glu Gln His Val Thr
50                  55                  60

Gln Leu Met Ser Thr Glu Pro Leu Pro Arg Thr Leu Ser Pro Thr Pro
65                  70                  75                  80

Ala Ser Ala Thr Ala Pro Thr Ser Gln Gly Ile Pro Thr Ser Asp Glu
                85                  90                  95

Glu Ser Thr Pro Lys Lys Ser Lys Ala Arg Ile Leu Glu Ser Ile Thr
            100                 105                 110
```

```
Val Ser Ser Leu Met Ala Thr Pro Gln Asp Pro Lys Gly Gln Gly Val
        115                 120                 125

Gly Thr Gly Arg Ser Ala Ser Lys Leu Arg Ile Ala Gln Val Ser Pro
    130                 135                 140

Gly Pro Arg Asp Ser Pro
145                 150

<210> SEQ ID NO 10
<211> LENGTH: 50
<212> TYPE: PRT
<213> ORGANISM: Homo sapiens

<400> SEQUENCE: 10

Thr Gln Cys Gln Leu Val Pro Val Val Glu Ile Gly Ile Ser Glu Arg
1               5                   10                  15

Gln Asn Ala Glu Gln His Val Thr Gln Leu Met Ser Thr Glu Pro Leu
                20                  25                  30

Pro Arg Thr Leu Ser Pro Thr Pro Ala Ser Ala Thr Ala Pro Thr Ser
            35                  40                  45

Gln Gly
    50
```

SCREENING METHOD OF ANTICANCER AGENT FOCUSED ON FUNCTION OF HP1 AND EVALUATION SYSTEM

TECHNICAL FIELD

The present invention relates to a method for evaluating chromosome instability, a method for screening for an anticancer agent using the evaluation method and an antibody for evaluating chromosome instability.

BACKGROUND ART

In cell division, the chromosome segregation process is the most fundamental phenomenon of life for maintaining homeostasis of multicellular organisms. More specifically, for ontogenesis and accurate transfer of genetic information to a next generation, chromosomes replicated in the cell division process must be accurately segregated without excess or deficiency.

It is considered that excess or deficiency in the number of chromosomes resulting from abnormal chromosome segregation will induce malignant traits. More specifically, in many cancer cells, a trait "chromosome instability" in which the number of chromosomes increases or decreases for every cell division, is observed, and thus aneuploidy is found which is the number of chromosomes changes from that of the original cell. Aneuploidy leads to increase the copy number of oncogene or decrease the copy number of tumor suppressor gene. Because of this, acquisition of chromosome instability is deeply related to acquisition of malignant trait of a cell (Non Patent Literature 1).

Chromosome instability further diversifies cancer cells and cancer cells having various chromosomal abnormalities increase. Diversification makes it difficult to treat cancer. Such cancer-cell diversification is a common feature observed in progressive cancers. It is considered that stabilizing chromosome or eliminating chromosome instability of cells leads to treating cancer. Then, it is expected to develop an anticancer drug using effective for a wide variety of progressive cancers focusing on chromosome instability. However, despite the clinical expectation, a mechanism for generating chromosome instability has not been sufficiently understood.

Cell division is a phenomenon occurring in a very short time-period during a cell cycle; however, in such a short time-period, chromosome segregation is dynamically and accurately controlled. Thus, individual processes of the cell division must be extremely precisely and timely controlled. At a molecular level, the cell-division processes are controlled with phosphorylation of a series of proteins by protein kinases and phosphatases. Particularly, a ubiquitous protein kinase, i.e., Aurora B, has been actively studied (Non Patent Literatures 2, 3). It is suggested that if the activity of Aurora B decreases, an essential function of cells to cancel incorrect attachment of microtubules to kinetochores is impaired, resulting in abnormal chromosome segregation. Thus, a decrease of Aurora B activity may be deeply involved in occurrence of abnormal chromosome segregation (Non Patent Literature 4).

Aurora kinase is serine/threonine kinase. In human cells, three types of Aurora kinases (Aurora A, B, C) are present having highly homologous region in the C-terminal kinase domains. Of them, Aurora B constitutes a chromosomal passenger complex (CPC), together with INCENP (Inner Centromere Protein), Survivin and Borealin/Dasra. Localization of CPC varies depending on the phases of cell division. CPC detects the binding between microtubule and kinetochore, controls activity of Aurora B to correct improper attachment of microtubule to kinetochore. In this manner, it is elucidated that CPC controls a series of processes from chromosome segregation to cell division. Particularly, as mentioned above, the microtubule-kinetochore binding is a key process for accurately segregating chromosomes, and the relevancy with chromosome instability of cancer cells attracts attention.

Aurora B is a constitutional element of CPC and considered to be involved in cancer-cell chromosome instability, as mentioned above. In addition, Aurora B is highly expressed in various cancer cells and high expression of Aurora B is connected to poor prognosis. Because of this, an Aurora kinase inhibitor attracts attention as a new candidate for an anticancer agent (Patent Literatures 1 to 3). Since the Aurora kinase inhibitor is considered to act only in a period of the cell division, it can act selectively on cancer cells restlessly repeating cell division. For the reason, cytotoxicity thereof to the normal-tissue cells rarely divided is considered to be low. Actually, among compounds developed as an Aurora kinase inhibitor, there are compounds like MNL8237 (alisertib) and VX-680 whose clinical trials as novel anticancer agents have been started (Patent Literatures 4, 5). However, it cannot be said that drug efficacies of the inhibitors are sufficient. This is because these inhibitors competitively bind to an ATP binding site of an Aurora kinase. Because of this, against expectation in the beginning of development, it is pointed out a possibility that the inhibitors may bind to ATP binding sites of other kinases except Aurora kinase and inhibit the functions.

CITATION LIST

Patent Literature

Patent Literature 1: National Publication of International Patent Application No. 2010-523534
Patent Literature 2: National Publication of International Patent Application No. 2015-520222
Patent Literature 3: International Publication No. WO 2014/112144
Patent Literature 4: International Publication No. WO 2008/063525
Patent Literature 5: International Publication No. WO 2008/013807 Non Patent Literatures
Non Patent Literature 1: Thompson, S. L. et al., 2010, Cuur. Biol., Vol. 20, R285-R295.
Non Patent Literature 2: Kelly, A. E., and Funabiki, H., 2009, Curr. Opin. Cell Biol., Vol. 21, p. 51-58.
Non Patent Literature 3: Carmena, M. et al., 2012, Nat. Rev. Mol. Cell Biol., Vol. 13, p. 789-803.
Non Patent Literature 4: Cimini, D. et al., 2006, Curr. Biol. Vol. 16, p. 1711-1718.
Non Patent Literature 5: Ainsztein, A. M. et al., 1998, J. Cell Biol., Vol. 143, p. 1763-1774.
Non Patent Literature 6: Kang, J. et al., 2011, Mol. Biol. Cell, Vol. 22, p. 1181-1190.
Non Patent Literature 7: Salimian, K. J. et al., 2011, Curr. Biol., Vol. 21, p. 1158-1165.
Non Patent Literature 8: DeLuca, K. F. et al., 2011, J. Cell Sci., Vol. 124, p. 622-634.
Non Patent Literature 9: Zaytsev, A. V. et al., 2014, J, Cell Biol., Vol. 206, p. 45-59.

Non Patent Literature 10: Brasher S. V. et al., 2000, EMBO J., Vol. 19, p. 1587-1597.

SUMMARY OF INVENTION

Technical Problem

The feature of cancer cells is that cells become out of control and keep growing. Because of the feature, if a chemotherapy focusing on chromosome instability of cancer cells can be achieved, the chemotherapy is expected to effectively work on a wide variety of progressive cancers. More specifically, based on the finding of cause of "chromosome instability", therapeutic approach is eliminating diversity of cancer cells whose chromosomes are unstable by leading suppression of cell growth or by inducing cell death. However, there is a poor understanding of the molecular mechanism of chromosome instability and a means for producing an effective molecularly targeted drug has not yet been present.

An object of the present invention is to provide a method for screening and a system for an anticancer agent capable of specifically targeting the cell division of cancer cells, by clarify the difference in cell division between cancer cells and normal cells.

The present inventors performed the dynamic structural analysis of CPC specific to mitotic phase. During the analysis, we have found that binding of HP1 (heterochromatin protein 1) to CPC plays an important role in chromosome segregation. Based on the finding, the present invention provides a method for screening for an anticancer agent, involving detecting the interaction between HP1 and CPC or a change in the interaction to evaluate the function of Aurora B in cancer cells, thereby screening for an anticancer agent for selectively targeting cell division of cancer cells having an improper Aurora B function. The embodiment also provides an antibody for specifically detecting phosphorylation of serine at position 92 of HP1a, thereby enabling quantitative and qualitative evaluation of the Aurora B function through the phosphorylation of HP1. The antibody can be used in various systems for evaluating chromosome instability.

Solution to Problem

The present invention provides a method for screening for an anticancer agent, using the function of Aurora B as an indicator, focusing on cancer-cell chromosome instability, regardless of the degree of expression level of Aurora B. The present invention relates to the following evaluation method, screening method and antibody.
(1) A method for evaluating chromosome instability, comprising determining Aurora B activity based on phosphorylation of HP1α and/or HP1γ as an indicator.
(2) The method for evaluating chromosome instability according to (1), wherein the phosphorylation of HP1α and/or HP1γ is phosphorylation of serine at position 92 of HP1α and/or phosphorylation of serine at position 83 of HP1γ.
(3) The method for evaluating chromosome instability according to (2), wherein the phosphorylation of serine at position 92 of HP1α and/or phosphorylation of serine at position 83 of HP1γ is detected by an antibody.
(4) A method for screening for an anticancer agent, comprising using a change of interaction or binding between HP1 and INCENP as an indicator.
(5) The method for screening for an anticancer agent according to (4), comprising a first step of selecting a compound based on the change of interaction or binding between HP1 and INCENP as an indicator, and a second step of measuring accuracy of chromosome segregation with the selected compound during cell division by imaging analysis.
(6) The method for screening for an anticancer agent according to (4) or (5), wherein the indicator for the change of interaction or binding between HP1 and INCENP is phosphorylation of serine at position 92 of HP1α and/or phosphorylation of serine at position 83 of HP1γ.
(7) The method for screening for an anticancer agent according to (6), wherein the phosphorylation of serine at position 92 of HP1α and/or phosphorylation of serine at position 83 of HP1γ is detected by an antibody.
(8) The method for screening for an anticancer agent according to (4), wherein the change of binding is a change of binding between HP1 and INCENP containing a sequence at positions 121 to 270 based on in vitro analysis.
(9) The method for screening for an anticancer agent according to (8), wherein the change of binding between HP1 and INCENP is analyzed by binding assay or alpha assay.
(10) An antibody for specifically recognizing phosphorylation of serine at position 92 of HP1a, or a functional fragment thereof.
(11) A method for using an antibody for specifically recognizing phosphorylation of serine at position 92 of HP1α and/or serine at position 83 of HP1γ, comprising detecting phosphorylation of HP1α and/or HP1γ to determine Aurora B activity and/or chromosome instability.
(12) The method for using an antibody according to (11), wherein the detection of phosphorylation of HP1α and/or HP1γ is performed by at least one of immunoblotting, immunoprecipitation and immunostaining.

Advantageous Effects of Invention

A molecularly targeted drugs for putting a burden on an improper chromosome segregation has not yet been developed. Conventional molecularly targeted drugs are therapeutic drugs suppressing a hyperactivated function (gain of function) involved in development of a disease. More specifically, conventional therapeutic drugs are obtained by identifying a driver gene involved in development of cancer and screening for an inhibitory drug for the gene. In contrast, according to the screening method of the present invention, a therapeutic drug can be obtained by targeting a molecule involved in loss of function of a cell. A drug for targeting "loss of function" of a cell is completely new concept for developing a molecularly targeted drug.

The compound selected by the screening method of the present invention serves as an anticancer agent based on a new concept "acting on chromosome instability". The anticancer agent may possibly act on cells which become non-responsive to conventional drugs because sensibility/dependency to a driver gene mutation declined and a signal of a cell growth factor was diversified. Because of this, the anticancer agent can act on any types of cancers, in other words, a wide variety of cancers including drug-resistant cancers.

BRIEF DESCRIPTION OF DRAWINGS

FIG. 1 The figures show the binding amount of HP1 to INCENP.

FIG. 2 The figures show the binding of each of HP1 subtypes to INCENP. FIG. 2A shows the binding of HP1 to INCENP in normal cell line RPE1 (human retinal pigment epithelial cells), and in HeLa cells (human cervical cancer cells). FIG. 2B shows localization of each of HP1 subtypes and INCNENP in the centromere.

FIG. 4 The figures show the function of HP1 in CPC.

FIG. 5 The figures show results of analysis on reactivity of an antibody (anti-HP1α-pS92) for specifically recognizing phosphorylation of Ser 92 of HP1. FIG. 5B shows inhibition of expression of HP1 by siRNA in the interphase; more specifically, when phosphorylation by Aurora B is inhibited by Aurora B inhibitor, ZM, an HP1α-pS92 antibody does not react. FIG. 5C shows specificity of the anti-HP1α-pS92 antibody. The anti-HP1α-pS92 antibody reacts to GFP-HP1α and endogenous HP1a, but does not react to GFP-HP1α S92A mutant obtained by substituting serine at position 92 with alanine. FIG. 5D shows that HP1α in the metaphase is detected by the anti-HP1α-pS92 antibody. FIG. 5E shows that HP1α localized in the centromere is detected by the anti-HP1α-pS92 antibody.

FIGS. 5F and 5G show that proteins constituting CPC are efficiently immunoprecipitated by the anti-HP1α-pS92 antibody. FIG. 5H shows correlation between phosphorylation of HP1α and activation of Aurora B. When CPC is immunoprecipitated by the anti-HP1α-pS92 antibody, the binding amount of HP1 is larger than the case where CPC is immunoprecipitated by an INCENP specific antibody (left panel). More HP1 binding to CPC shows higher Aurora B activity (right panel).

FIG. 6 The figures show that binding of HP1 to INCENP enhances and maintains the kinase activity of Aurora B, suggesting that HP1 is an allosteric factor of activating Aurora B. FIG. 6A shows a schematic diagram of INCENP mutants not binding to HP1 (FIG. 6A, left panel), and the immunoprecipitation from INCENP mutant (FIG. 6A, right panel).

FIG. 9 The figures show that the binding of HP1 to CPC is required in accurate chromosome segregation in normal cells.

DESCRIPTION OF EMBODIMENTS

Figure 1A:
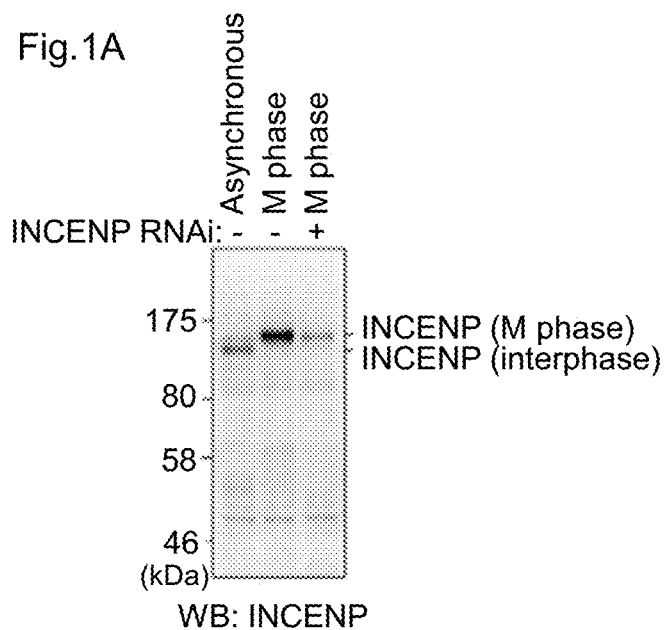
FIG. 1A shows the specificity of an anti-INCENP antibody used in a CPC immunoprecipitation experiment.

The present inventors have specifically analyzed chromosome segregation associated with cell division. As a result, they have found that an allosteric effect produced by the binding of HP1 to CPC is indispensable for properly functioning Aurora B, thereby ensuring accurate chromosome segregation. Based on the finding, the present invention was accomplished. The present inventors have found the difference in cell division between cancer cells and normal cells at a molecular level. Taking advantage of the understanding of molecular-level difference, an anticancer agent can be screened.

In the method for evaluating the chromosome instability according to the present invention, activation of Aurora B can be evaluated based on the phosphorylation degrees of HP1α or γ as an indicator. Thus, unlike conventional anticancer agents obtained by simply focusing on only quantitative difference in Aurora B, an anticancer agent that specifically acts on a wide variety of cancer cells can be obtained. Particularly, if a hit compound is selected by high throughput screening (HTS) and further analyzed by live-imaging analysis, it can be determined whether or not the compound increases abnormal chromosome segregation to induce cell death in a cancer-cell specific manner. In this manner, compounds that specifically act on cancer cells can be selected.

As a screening method for an anticancer agent according to the present invention, any method may be employed as long as a compound influencing the interaction between HP1 and CPC and a change in binding can be screened. The "change in binding" herein refers to not only a quantitative change but also a qualitative change including a change in phosphorylation degree of HP1, a change in binding amount to INCENP and a change in localization. For example, a compound influencing the interaction with INCENP to which HP1 directly binds can be screened by HTS. Since the binding region of HP1 with INCENP has already analyzed, expression systems of E. coli or cultured cells expressing the region can be used. Since the present inventors already constructed systems in which binding of HP1 and INCENP can be analyzed by binding assay and alpha assay, compounds can be screened by use of the systems.

It was found that, in the cancer cells having chromosome instability, the binding of HP1 and INCENP decreases; whereas, in cultured cells having chromosome stability and maintaining a diploid state, the binding of HP1 and INCENP tends to high. Accordingly, a compound differently acting on these two types of cultured cells can be screened.

In cancer cells, there is a possibility that the action of a compound differs depending on the amount of endogenous HP1 and expression level of Aurora B. Then, if the candidate compounds obtained by HTS are subjected to a cell-level evaluation study, more specifically, measuring frequency of chromosome segregation errors based on observation of images of dividing cells, the candidate compounds can be further selected.

The present inventors have found that the binding of HP1 to CPC is required for sufficient activation of Aurora B. They further have found that in HP1α bound to CPC when Aurora B is activated, a serine residue at position 92 therein is phosphorylated. An antibody (HP1α-pS92 antibody) for specifically recognizing the phosphorylation can also serve as a tool for evaluating the action of Aurora B within a cell. Since the binding of HP1α to CPC in the mitotic phase and activation of Aurora B correlate with phosphorylation of HP1α, the antibody can be used for evaluating not only phosphorylation of HP1α but also functions of CPC and Aurora B.

More specifically, analysis may be carried out by treating cultured cells with each of the candidate compounds, and then, detecting activation of Aurora B in M-phase by the antibody for specifically recognizing phosphorylation of HP1α. Further, cancer cells and normal diploid cells are treated with each of the compounds exerting an effect on activation of Aurora B, and the drug potency of each of the compounds may be evaluated based on a cell growth curve or a change in the dead-cell. If cancer cells specifically exhibit sensitivity to a compound, the cancer cells are treated with the compound and images of the cell division are observed by live-imaging to examine, e.g., the presence or absence of lethal chromosome missegregation, a cause for suppressing cell growth can be determined. As the live-imaging used herein, any method may be used as long as the state of chromosome segregation can be visually measured; for example, a method, which includes preparing cells by labelling chromosomes thereof with fluorescence substance, automatically taking time-lapse images of cell division by use of 4D confocal inverted fluorescence microscope, and comprehensively analyzing the moving states of chromosomes, can be mentioned.

The screening method is based on a mechanism that is not directed to correcting the function of cancer cells causing abnormal chromosome segregation but directed to further worsening the abnormality of cancer cells having abnormal chromosome segregation due to defective binding of HP1-CPC. By further worsening the abnormality, cancer cells are led to cell death, with the result that the cancer cells are killed. In other words, the screening method is based on a mechanism derived from the new finding by the present inventors. Accordingly, the effect on normal cells having no chromosome missegregation due to sufficient HP1-CPC binding is expected to be low. In this manner, a compound for specifically targeting cell division of cancer cells can be obtained.

Most of conventional anticancer agents are directed to inhibiting a factor excessively expressed in cancer cells, thereby exhibiting an anticancer activity. The conventional anticancer agents give damage to normal cells containing the factor at a lower expression level than in cancer cells for maintaining cell function. Thus, serious side effects (more specifically, leukopenia, depilation, vomiting and general malaise at clinical sites) are mostly concerned. However, the compound for augmenting chromosome instability selected based on the mechanism of the present invention further puts a load on cell-division abnormality, which is characteristically worsened in cancer cells, to lead the cancer cell death. In this case, it is expected that the adverse effect of the compound on normal cells may be low, because the function of is maintained at a high level in normal cells. Thus, finding of a compound providing few side effects compared to conventional anticancer agents can be expected.

HP1 has three subtypes α, β and γ, it has been reported that HP1γ also has a site to be phosphorylated by Aurora B during cell division. Based on the homology of amino acid sequence around serine at position 92 of HP1α, Ser83 of HP1γ is considered to be a phosphorylation site. Accordingly, an antibody for specifically recognizing phosphorylation of serine of HP1γ can be used similarly to the antibody recognizing phosphorylation of serine at position 92 of HP1α. The antibody for specifically recognizing phosphorylation of serine at position 83 of HP1γ can be produced by the method described in the specification of the present invention or a method known in the art.

In the present invention, as the antibody recognizing phosphorylation of serine at position 92 of HP1α, a polyclonal antibody obtained by immunizing rabbits is used; however, any antibody may be used as long as it can recognize phosphorylation of the above site. More specifically, examples of the antibody of the present invention include a monoclonal antibody recognizing phosphorylation of serine at position 92 of HP1α and a functional fragment of the antibody. Examples of the functional fragment of the antibody include functional fragments of antibodies, such as Fab, Fab', F (ab')$_2$, single-strand antibody (scFv) and disulfide stabilized V-region fragment (dsFv) or a CDR-containing peptide. The functional fragment of an antibody can be obtained by a method known in the art such as digestion with an enzyme such as pepsin or papain.

Now, the present invention will be more specifically described while mentioning the action of HP1 in detail. First, e.g., reagents and methods used herein will be roughly described.

(1) Antibody

Antibodies prepared in the present invention are as follows. An INCENP antibody was prepared by immunizing rabbits with a synthetic peptide C+DLEDIFKK-SKPRYHKRTSS (SEQ ID NO: 1, amino acids at positions 876 to 894) and purified based on affinity for antigen. An antibody for specifically recognizing phosphorylation of serine at position 92 of HP1α was prepared by immunizing rabbits with a synthetic peptide C+NKRK(pS)NFSNS (SEQ ID NO: 2, amino acids at positions 88 to 97). The obtained antibody was purified based on affinity by using a column of phosphorylated peptide or non-phosphorylated peptide. Commercially available antibodies will be described in sequence.

(2) Cell Culture

HeLa (cervical cancer cell line), RPE1 (retinal pigment epithelial cell line), TIG-3 (fetal lung-derived cell line), U2OS (osteosarcoma cell line), HT-1080 (fibrosarcoma cell line), A549 (alveolar basal epithelial adenocarcinoma cell line), BJ (fibroblast cell line), MIA PaCa-2 (pancreatic cancer cell line), HCT116 (colon adenocarcinoma cell line) and DLD-1 cells (colon adenocarcinoma cell line) cells were cultured in DME medium; H522 (lung adenocarcinoma cell line) and PK45H cells (pancreatic cancer cell line) were cultured in RPMI-1640; and LoVo cells (colon cancer cell line) were cultured in HamF12, by adding 10% FCS, 0.2 mM L-glutamine, 100 U/ml penicillin and 100 μg/ml streptomycin to each medium, under 5% $CO_2$ at 37° C.

(3) RNAi

The target sequences (manufactured by Invitrogen) of siRNA are as follows:

```
INCENP (ORF):
                              (SEQ ID NO: 3)
5'-CAGUGUAGAGAAGCUGGCUACAGUG-3'

HP1α (5' UTR):
                              (SEQ ID NO: 4)
5'-CCUUAGUCUUUCAGGUGGAACGGUG-3'

HP1α (ORF):
                              (SEQ ID NO: 5)
5'-UAACAAGAGGAAAUCCAAUUUCUCA-3'

HP1β (ORF):
                              (SEQ ID NO: 6)
5'-GGAUAAGUGUUUCAAGGCAACCUUU-3'

HP1γ (ORF):
                              (SEQ ID NO: 7)
5'-UCUUAACUCUCAGAAAGCUGGCAAA-3'
```

Introduction of siRNA was carried out by an RNAi MAX transfection reagent (manufactured by Invitrogen) in an antibiotic substance-free culture medium. As a control, $H_2O$ alone was added to the same medium. Cell lines HeLa, HT-1080, A549, HCT116 and DLD-1 were transfected with 50 nM siRNA oligonucleotide; whereas, cell lines U2OS, RPE1 and TIG-3 were transfected with 20 nM siRNA oligonucleotide.

(4) Immunoblotting

Cells were dissolved in an immunoprecipitation buffer, which was prepared by adding, to a solution containing 20 mM Tris (pH7.4), 100 mM NaCl, 20 mM β-glycerophosphate, 5 mM $MgCl_2$, 1 mM NaF, 0.1% Triton X-100, 10% glycerol, 1 mM DTT and 0.1 μM okadaic acid, a protease inhibitor (Complete EDTA-free, manufactured by Roche). SDS-PAGE was carried out and transferred to PVDF membrane. A primary antibody diluted in Can Get Signal Immunoreaction Enhancer Solution 1 (manufactured by TOYOBO), HRP labeled secondary antibody (manufactured by Amersham) were used. Analysis was carried out based on chemiluminescence by luminol and coumaric acid (manufactured by Sigma). Images were taken by ChemDoc XRS (manufactured by Bio-Rad) and analyzed by Quality One software (manufactured by Bio-Rad).

(5) Immunoprecipitation Method

The cells in the mitotic phase were incubated in a solution, which was prepared by adding 1 U/μl OmniCleave Endonuclease (manufactured by Epicentre) in the above immunoprecipitation buffer, at 4° C. for 30 minutes. The solution was centrifuged at 4° C. and 15,000 rpm for 10 minutes and the supernatant was further centrifuged. The resultant supernatant was used for immunoprecipitation. Protein A-Sepharose (manufactured by Bio-Rad) having an antibody bound thereto, was allowed to react with cell extracts and subjected to immunoprecipitation. The sample obtained by immunoprecipitation was subjected to the immunoblotting using peroxidase-labeled Mouse TrueBlot ULTRA or Rabbit TrueBlot (manufactured by eBioscience) as a secondary antibody.

(6) Immunostaining Method

Cells were cultured on a cover glass and immobilized with 4% paraformaldehyde in PHEM buffer solution (60 mM PIPES, 25 mM HEPES, 10 mM EGTA, 2 mM $MgCl_2$, pH7.0) or PBS, at room temperature. Cells were treated with the above buffer solution containing 0.2 to 1.0% Triton X-100, and blocked with a 3% BSA-containing buffer. Images were obtained by AxiolmagerM1 miacroscope (manufactured by Zeiss) equipped with CoolSNAP HQ camera (manufactured by Photometrics) operated by MetaMorph software (manufactured by MDS Analytical Technologies). The intensity of fluorescence was analyzed by ImageJ software (National Institute of Health).

(7) In Vitro Kinase Assay

The kinase assay was carried out by adding a substrate in a kinase buffer (20 mM Tris-HCl, 50 mM $MgCl_2$, 100 mM NaCl, 20 μM ATP, pH7.5) and 0.2 mCi/ml[γ-$^{32}$P]ATP. As the substrate, GST-Hec1 (1-80) or recombinant histones H3 (manufactured by New England Biolas) was used. Twenty nM INCENP and 120 nM GST-Aurora B were reacted in the presence or absence of 1 μM HP1 at 30° C. for 20 minutes and the reaction was terminated by Laemmli sample buffer. Phosphorylation was analyzed by Typhoon scanner (manufactured by GE Healthcare) and a liquid scintillation counter.

Note that, hereinafter, unless otherwise specified, analysis was carried out in accordance with the above method and a standard method in this field.

1. Amount of HP1 Bound to CPC

It has been known that HP1 binds to CPC via binding to INCENP; however, significance of the interaction to CPC function has not been elucidated (Non Patent Literatures 5, 6). From the results of fluorescence microscopic observation, it has been found that HP1 localizes in the centromere during the mitosis, similarly to CPC. Then, the interaction between CPC and HP1 was analyzed by immunoprecipitation (FIG. 1).

FIG. 1A shows the extracts obtained from asynchronous HeLa cells (Asynchronous), M-phase HeLa cells, and M-phase HeLa cells 48 hours after introduction of INCENP siRNA, were immunoblotted with INCENP-specific antibody (P240, manufactured by Cell Signaling Technology). It was found that the amount of INCENP decreases by RNAi, and that the mobility of INCENP in the M-phase is low compared to INCENP of asynchronous HeLa cells since the INCENP in the M-phase is phosphorylated.

Figure 1B:
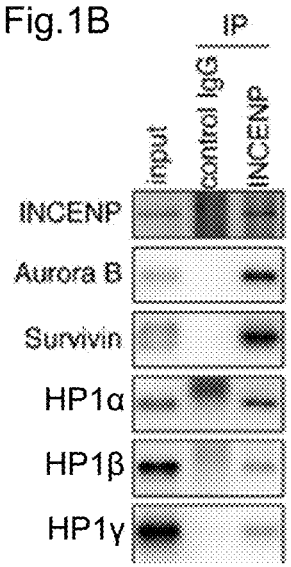
FIG. 1B shows binding of each of Aurora B, Survivin and HP1 subtypes (α, β, γ) and INCENP.

Next, whether or not binding to INCENP differs among the subtypes of HP1 was analyzed (FIG. 1B). HP1 has three subtypes, α, β and γ. Mitotic HeLa cell extracts were subjected to immunoprecipitation with an INCENP antibody or control IgG and then analyzed by immunoblotting using antibodies against INCENP, Aurora B (clone 6, manufactured by BD Bioscience) and Survivin (71G4B7E, manufactured by Cell Signaling Technology) constituting CPC; an HP1α antibody (clone 15.19s2, manufactured by Millipore), an HP1β antibody (clone 1MOD-1A9, manufactured by Millipore) and an HP1 γ antibody (clone 2MOD-1G6, manufactured by Millipore). It was found that not only HP1α but also HP1β and γ are bound to CPC in the M-phase.

Figure 1C:
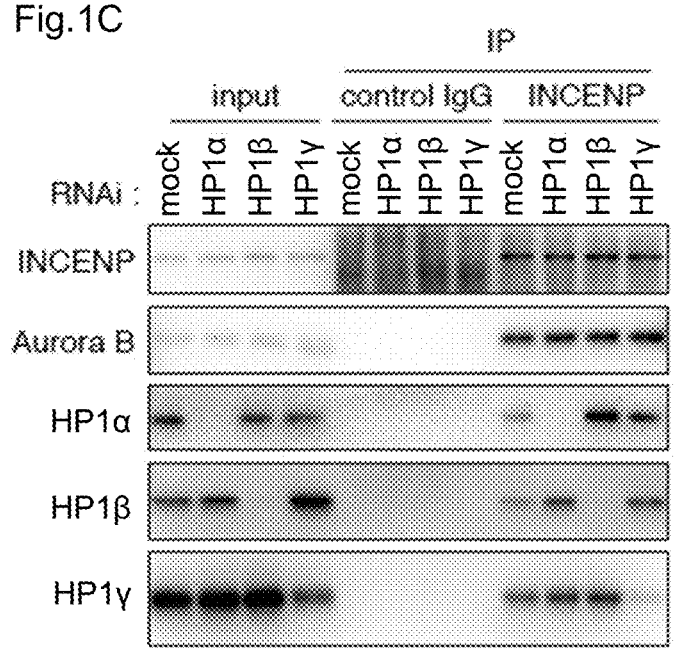
FIG. 1C shows the analysis results on binding between INCENP and each of HP1 subtypes whose expression is suppressed by siRNA.

Further, in the HeLa cells, expression of each of the subtypes of HP1 was suppressed by RNAi. Mitotic HeLa cell extracts were subjected to immunoprecipitation with an INCENP antibody and control IgG and analyzed by immunoblotting using the antibodies of the subtypes of HP1, in the same manner as above. It was found that if the expression of a subtype of HP1 was inhibited by RNAi; instead, binding amounts of other subtypes of HP1 to INCENP increase (FIG. 1C).

Figure 1D:
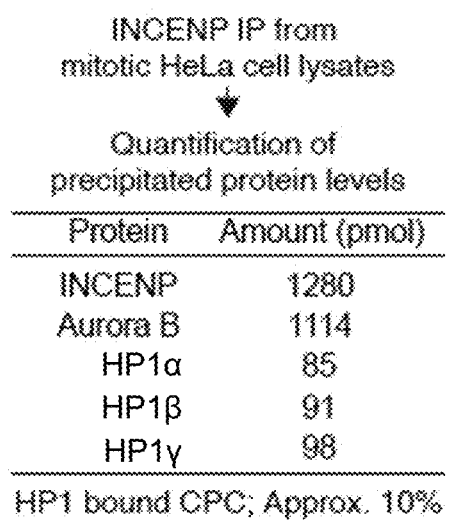
FIG. 1D shows the results of quantitative analysis on binding between each of HP1 subtypes to CPC.

Quantitative analysis was carried out using purified recombinant HP1-subtype proteins. As a result, it was found that, in the M-phase HeLa cells, about 10% of CPC is bound to HP1 (FIG. 1D).

2. Difference in Binding Amount of M-Phase HP1-Subtypes to CPC in Malignant Transformed Cells or Non-Transformed Cells It is reported that function to reduce the error in chromosome segregation via Aurora B is more stable in non-transformed diploid cells, i.e., retinal pigment cell line, RPE1 compared to HeLa cells (Non Patent Literature 7). Then, whether or not the binding of HP1 to CPC is correlated with the segregation error was analyzed by using these two types of cell lines.

Extracts from M-phase RPE1 cells and HeLa cells were subjected to immunoprecipitation with INCENP antibody and analyzed by immunoblotting with antibodies against INCENP, Aurora B, Survivin and Borealin constituting CPC (manufactured by Novus Biologicals) and antibodies against the subtypes of HP1. In the lower histogram of FIG. 2A, the amounts of HP1 subtypes coprecipitated with INCENP are shown based on the amounts of those in RPE1 cells as 1.0. As a result, it was found that the amount of HP1 bound to CPC in RPE1 cells is 2 to 4 times as large as that in HeLa cells, though no significant difference was observed in expression of each of HP1 subtypes between two cells. Thus, it was demonstrated that HP1-CPC binding does not depend on the expression level of HP1.

Furthermore, whether the amount of HP1 bound to CPC is correlated with the amount of HP1 localized in the centromere was analyzed by fluorescence microscope (FIG. 2B). Mitotic RPE1 cells and HeLa cells were co-stained with HP1α (MAB3584, manufactured by Chemicon), β, or γ and INCENP antibodies, and analyzed. The intensities of staining with HP1α, β or γ antibodies were normalized to the intensity of staining with INCENP and displayed as the histogram (FIG. 2B, lower graph). The histogram shows the results of analysis of 140 or more centromeres of 4 cells. It was shown that the fluorescence intensity of HP1 localized in the centromere of HeLa cells is distinguishably low compared to that in RPE1 cells.

3. Binding of HP1 to CPC in Various Cancer Cell Lines

Figure 3A:
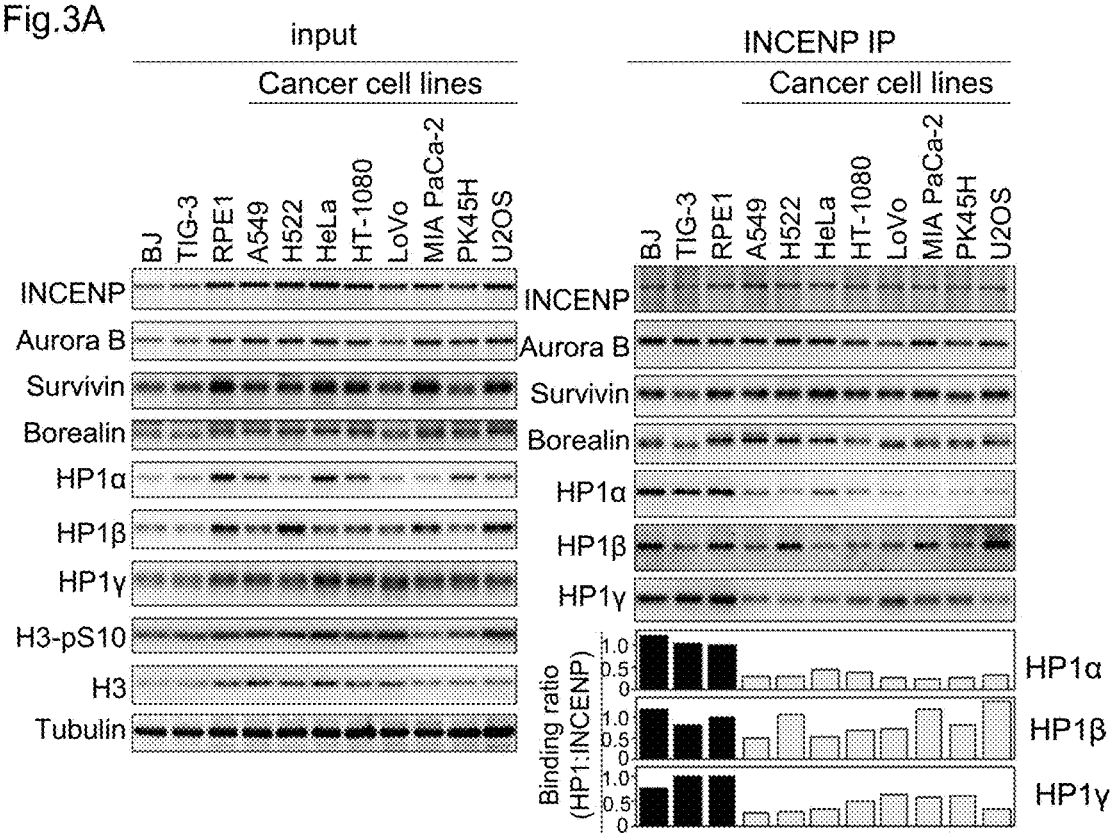
FIGS. 3A, B show the amounts of HP1 subtypes bound to INCENP in normal cell lines and cancer cell lines. In the cancer cell lines, it is shown that the amounts of HP1 subtypes binding to INCENP all reduce.

Next, the amounts of HP1 bound to CPC in various types of cancer cell lines were analyzed. More specifically, the amounts of HP1α, β, γ bound to CPC in cell lines derived from normal cells and cancer cells were analyzed. As cell lines derived from human non-transformed cells, BJ (fibroblast cell line), TIG-3 (fetal lung-derived cell line) and RPE1 (retinal pigment epithelial cell line) were used. As the cancer cell lines, A549 (alveolar basal epithelial adenocarcinoma cell line), H522 (lung adenocarcinoma cell line), HeLa (cervical cancer cell line), HT-1080 (fibrosarcoma cell line), LoVo (colon cancer cell line), MIA PaCa-2 (pancreatic cancer cell line), PK45H (pancreatic cancer cell line) and U2OS (osteosarcoma cell line) were used. Cell extracts of these cell lines were prepared and subjected to immunoprecipitation with an anti-INCENP antibody. The amounts of INCENP, Aurora B, Survivin, Borealin and subtypes of HP1 coprecipitated were examined. The results are shown in FIG. 3A. The histogram shows the amounts of HP1 subtypes coprecipitated with INCENP, and the amount of those in RPE1 cells is set to 1.0, similarly to FIG. 2A.

The subunits constituting CPC; INCENP, Aurora B, Survivin and Borealin, are coprecipitated equally, regardless of non-transformed cells and cancer cells. In contrast, the amounts of subtypes of HP1 bound to CPC are significantly low in all cancer cells compared to the non-transformed cells.

Figure 3B:
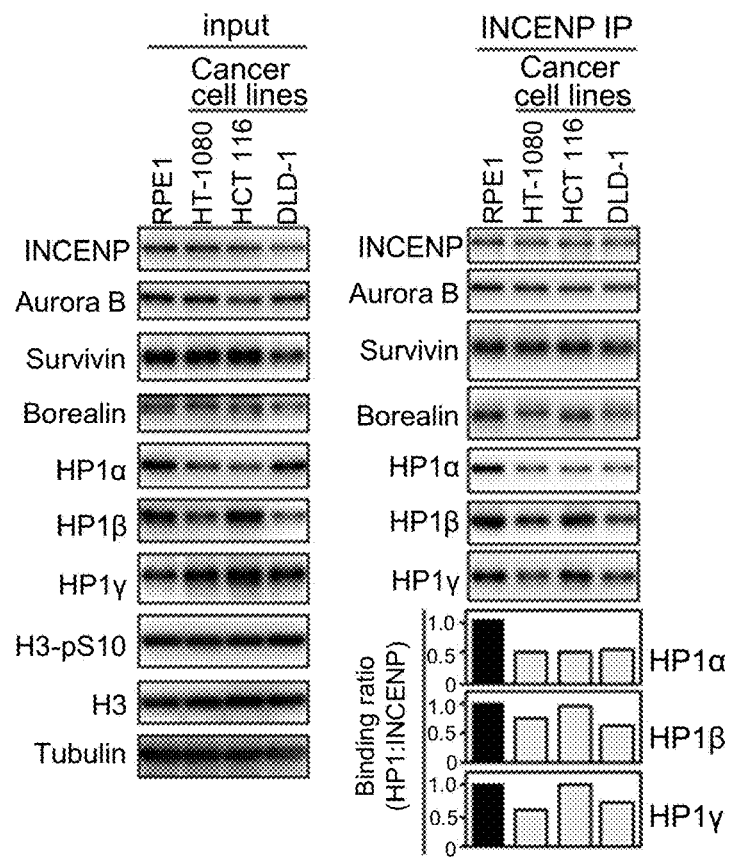
FIG. 3 The figures show the binding amount of each of HP1 subtypes to CPC in M-phase varied depending on with or without malignant transformation.

HCT116 and DLD-1 (both are human colon adenocarcinoma cell lines), which are known to show modest chromosome missegregation rates, were subjected to the similar analysis (FIG. 3B). It was found that binding of HP1 to INCENP is low even in HCT116 and DLD-1 cells having relatively low chromosome missegregation rate in the same as in other cancer cell lines exhibiting chromosome instability. Accordingly, it was suggested that a quantitatively sufficient amount of binding of HP1 to INCENP is required for suppressing chromosome missegregation.

This means that if a substance which influences the interaction between HP1 and CPC can be obtained, the substance can serve as a medical agent effective for a wide variety of cancers. More specifically, since cancer cells having chromosome instability, the binding of HP1 and INCENP is low, if the binding can be further reduced, chromosome instability is further augmented. With the result that cell death of the cancer cells can be induced or cell division can be terminated. Note that, the percentage of causing chromosome missegregation was 5% or less in the RPE1 cell line, about 30% in HT-1080 cell line where chromosome segregation is unstable and about 8% in HCT116 and DLD-1 cell lines where chromosome missegregation rates are relatively low.

4. Function of HP1 in CPC

Figure 4A:
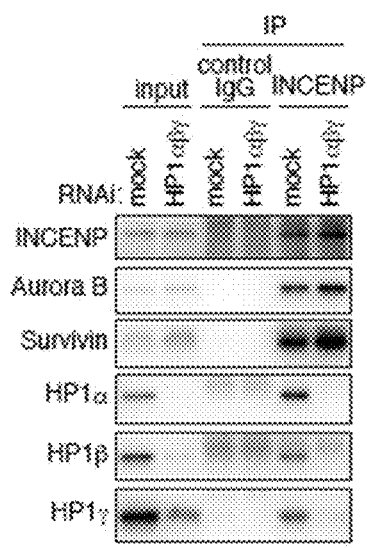
FIG. 4A shows the effect of suppressed HP1 expression on a complex formation of CPC.

To analyze functional importance of the binding of HP1 to CPC, all subtypes of HP1 were depleted with RNAi and complex formation of CPC was analyzed (FIG. 4A). After transfection of siRNA was performed, immunoprecipitation was carried out with INCENP antibody or control IgG, then INCENP, Aurora B and Survivin constituting CPC and HP1 subtypes were analyzed by immunoblotting. As a result, it was found that even if expression of all HP1 subtypes is depleted, complex formation of CPC is not virtually affected.

Figure 4B:
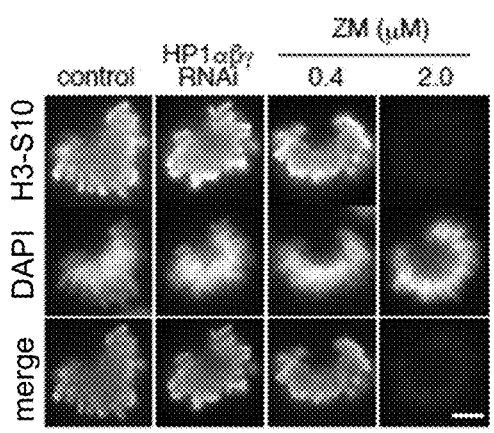
FIGS. 4B to 4D show the effect of HP1 suppressed in expression on phosphorylation of substrates of Aurora B (H3, Hec1, Dsn1). Phosphorylation by Aurora B is suppressed by RNAi of HP1 or an Aurora B inhibitor (ZM).

Next, activation of Aurora B was analyzed based on degree of phosphorylation of a substrate. HeLa cells were transfected with siRNA of all subtypes of HP1 to inhibit expression of all HP1 subtypes. Then, HeLa cells were treated with low concentration (0.4 μM) or high concentration (2.0 μM) of an Aurora B inhibitor, ZM447439 (ZM, manufactured by Tocris) and subjected to analysis. The cells were immobilized and then analyzed by a fluorescence microscope using an antibody recognizing phosphorylation of serine at position 10 of histone H3 (H3-pS10, 6G3, manufactured by Cell Signaling Technology) (FIG. 4B); an antibody recognizing phosphorylation of serine at position 44 of Hec1 (Hec1-pS44, Non Patent Literature 8); an Hec1 antibody (9G3.23, manufactured by Novus Biologicals) (FIG. 4C); and an antibody recognizing phosphorylation of serine at position 100 of Dsn1 (Dsn-pS100, Non Patent Literature 9) (FIG. 4D). Since phosphorylation status in phosphorylated Hec1 and Dsn1 were hardly distinguished, fluorescence intensities thereof were normalized to Hec1 and displayed as a histogram. In each sample, 150 or more centromeres of 10 cells were analyzed and displayed as a histogram.

Figure 4C:
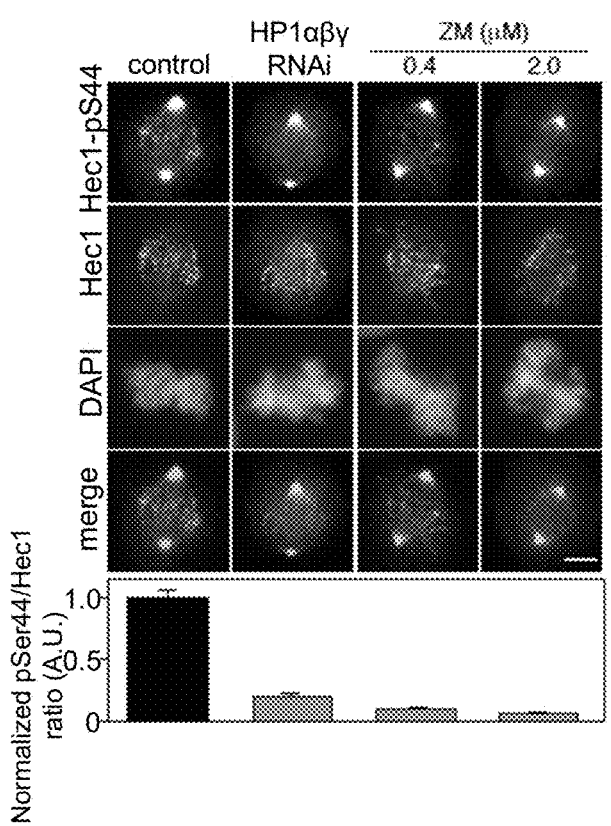
Figure 4D:
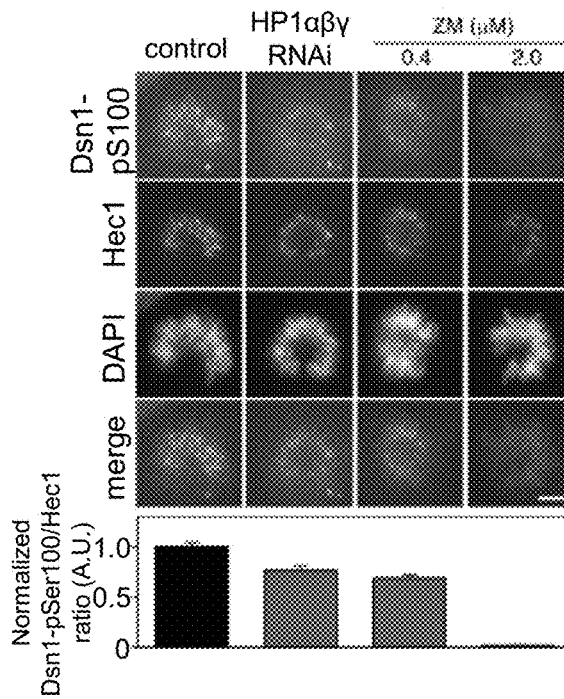

Histone H3 (Ser10) (FIG. 4B) and CENP-A (Ser7) (not shown), which are known as substrates of Aurora B, were not virtually affected by depletion of HP1; however, phosphorylation of Hec1 (Ndc80 complex) and Dsn1 (Mis12 complex), which are substrates of Aurora B present in the centromere, were significantly suppressed (FIGS. 4C, D).

The treatment with low-concentration ZM447439 has the suppressive effect equal to the effect produced by depletion of HP1 on phosphorylation of Hec1 and Dsn1. From this, it was suggested that activation of Aurora B is suppressed by depletion of HP1.

5. Specificity of Antibody (Anti-HP1α-pS92 Antibody) Recognizing Phosphorylation of Serine at Position 92 of HP1α, and Correlation Between the Binding of HP1 to CPC and Aurora B Kinase Activity Whether activity of Aurora B is affected by HP1 was analyzed. An antibody for specifically detecting phosphorylation of serine at position 92 of HP1 (hereinafter referred to as an anti-HP1α-pS92 antibody) was used in the analysis.

Figure 5A:
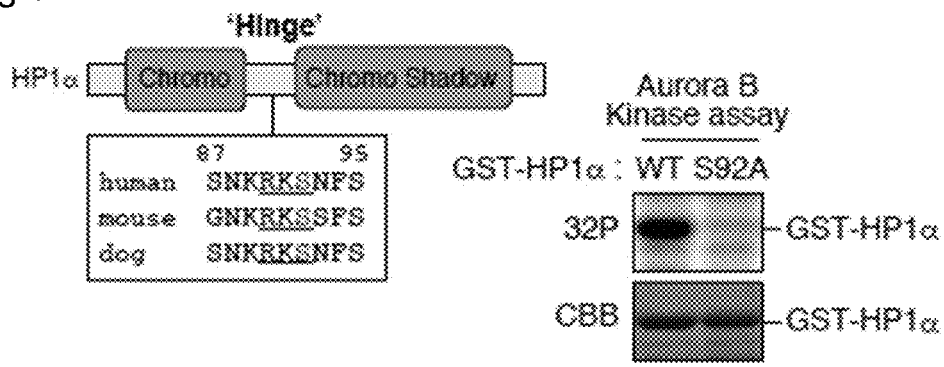
FIG. 5A schematically shows a region around serine at position 92 of HP1α. If serine is present at position 92, serine is phosphorylated by Aurora B; however a mutant S92A obtained by substituting serine with alanine, is not phosphorylated.

The anti-HP1α-pS92 antibody was prepared by immunizing rabbits with synthetic peptide C+NKRK(pS)NFSNS (prepared based on the sequence of human HP1α). FIG. 5A schematically shows a region containing the 92nd residue (serine) of HP1α to be phosphorylated in the mitotic phase. This region is present in the hinge region of HP1α and conserved within species (FIG. 5A, left panel). A S92A mutant (prepared by substituting serine at position 92 with alanine) significantly inhibits phosphorylation by Aurora B (FIG. 5A, right panel). HP1γ has serine to be phosphorylated by Aurora B at position 83 within the homologous region (not shown herein). It is considered that serine at position 83 of HP1γ has the same significance as serine at position 92 of HP1α.

Figure 5B:
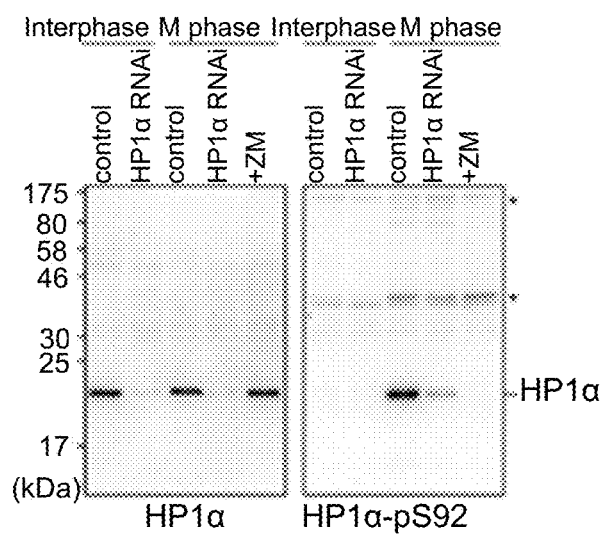
FIGS. 5B, 5C and 5D show the results of examination on specificity of an anti-HP1α-pS92 antibody.

In the following part, we will describe on specificity of the anti-HP1α-pS92 antibody, and that if the antibody is used in immunoprecipitation, immunoblotting and immunostaining, phosphorylated HP1α can be sensitively detected. The cells where the expression of HP1α was suppressed by RNAi or where the activation of Aurora B was inhibited by an Aurora B kinase inhibitor, were treated with thymidine or nocodazole to obtain the cells conditioned in the interphase or metaphase. Cell extracts were obtained from the cells and subjected to analysis. Analysis was carried out by immunoblotting using HP1α antibody and anti-HP1α-pS92 antibody (FIG. 5B). The HP1α antibody detects HP1α except the case where the expression of HP1α is suppressed by RNAi, regardless of the interphase or metaphase and the presence or absence of Aurora B activity; whereas in the blot using the anti-HP1α-pS92 antibody, a band was detected only in the metaphase cells where Aurora B is activated. Thus, it is shown that not only phosphorylation of HP1α can be specifically detected by the anti-HP1α-pS92 antibody but also the activation of Aurora B can be specifically detected based on phosphorylation at position 92 of HP1α as the indicator.

Figure 5C:
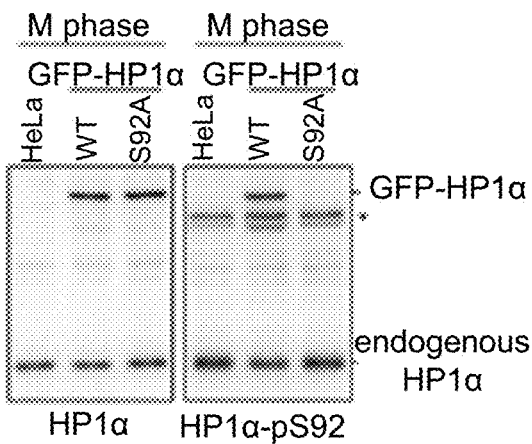

The anti-HP1α-pS92 antibody specifically recognizes phosphorylation at position 92 of HP1α and does not recognize a mutant which is substituted serine at position 92 with alanine. GFP-HP1α WT (WT), which is a fusion of wild type HP1α and GFP protein, and GFP-HP1α S92A, which is a fusion of mutant HP1α (obtained by substituting serine at position 92 with alanine, S92A) and GFP protein, were introduced into HeLa cells. Cell extracts from metaphase cells were analyzed by immunoblotting (FIG. 5C).

Since the mutant (obtained by substituting serine at position 92 with alanine) is not phosphorylated even in the metaphase, the anti-HP1α-pS92 antibody does not recognize the mutant. Only phosphorylated HP1α is specifically detected.

Figure 5D:
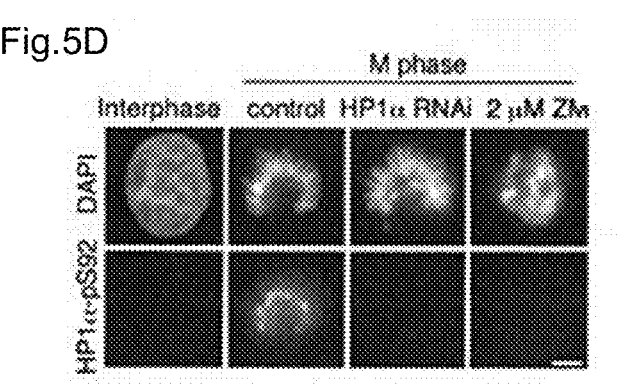

It was shown that the anti-HP1α-pS92 antibody sensitively detects phosphorylated HP1α even if it is used in immunostaining (FIGS. 5D, E). Cells of the interphase, cells of the metaphase, cells of the metaphase where the expression of HP1α was depleted by siRNA and cells of the metaphase where the activity of Aurora B was suppressed by ZM447439 were immunostained with an anti-HP1α-pS92 antibody (FIG. 5D). Only the metaphase cells used as the control were stained. In the interphase cells, cells where the expression of HP1α was depleted and cells where the activity of Aurora B was suppressed, phosphorylated HP1α was not detected.

It was also shown that phosphorylated HP1α is localized only in the centromere by immunostaining (FIG. 5E). Immunostaining clearly shows that HP1α having phosphorylated serine at position 92 is localized in the centromere similarly to Aurora B.

It was shown that when immunoprecipitation is carried out with the anti-HP1α-pS92 antibody, INCENP Aurora B, Survivin and Borealin constituting CPC, and other HP1 subtypes, are coprecipitated (FIGS. 5F, G). When immunoprecipitation is carried out with the anti-HP1α-pS92 antibody, Aurora B, Survivin and Borealin constituting CPC are coprecipitated in the same manner as in immunoprecipitation with the INCENP antibody. In contrast, when immunoprecipitation was carried out with HP1α, the amounts of these proteins constituting CPC to be coprecipitated are significantly low (FIG. 5F). When the expression of HP1α and INCENP is depleted by RNAi, the amounts of proteins constituting CPC to be coprecipitated with the anti-HP1α-pS92 antibody are significantly low (FIG. 5G).

As shown in the above, the anti-HP1α-pS92 antibody specifically recognizes phosphorylation of serine at position 92 and can be used for various analyses including immunoblotting, cell staining and immunoprecipitation (FIGS. 5B to G). In particular, since HP1α captured by the anti-HP1α-pS92 antibody selectively recognizes HP1α bound to CPC, activation of Aurora B, particularly activation thereof when CPC is localized in the centromere, can be sensitively detected. More specifically, phosphorylated HP1α can be conveniently used as an excellent tool reflecting the activity of Aurora B.

Next, we will describe that the binding of HP1 to CPC is necessary for activating Aurora B. Immunoprecipitation was carried out with anti-HP1α-pS92 antibody and INCENP antibody and proteins constituting CPC and subtypes of HP1 were analyzed by immunoblotting (FIG. 5H, left panel). As a result, in the case where immunoprecipitation was carried out with the anti-HP1α-pS92 antibody, proteins constituting CPC were coprecipitated similarly to the case of immunoprecipitation with INCENP. Further, it was shown that the kinase activity of Aurora B is significantly high in the fractions immunoprecipitated with the anti-HP1α-pS92 antibody, compared to the fractions obtained by immunoprecipitation with the INCENP antibody (FIG. 5H, right panel). The results suggest that the binding of HP1 to CPC is necessary for activation of Aurora B. Furthermore, the kinase activities of the fractions obtained by immunoprecipitation with the anti-HP1α-pS92 antibody and the INCENP antibody were both inhibited by addition of Aurora B inhibitor, ZM447439. From this, it was confirmed that the kinase activity of the fraction immunoprecipitated with the anti-HP1α-pS92 antibody is due to Aurora B.

6. Binding of HP1 to INCENP and Activation of Aurora B

Figure 6B:
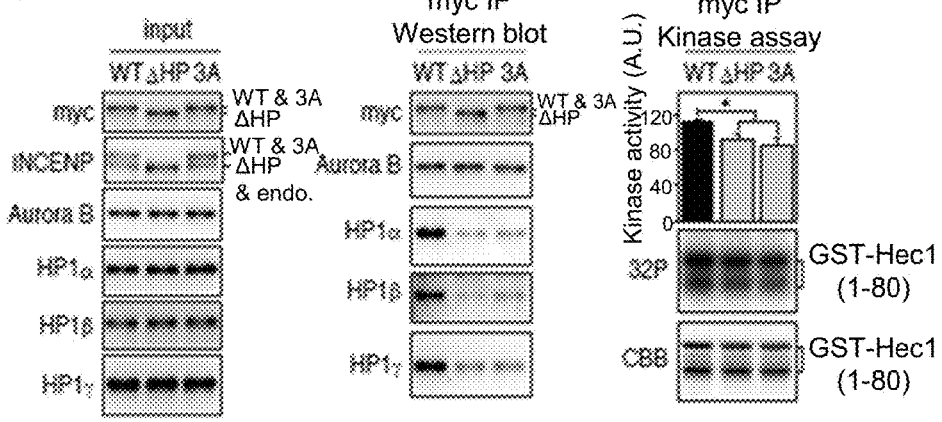
FIG. 6B shows that the Aurora B kinase activity is suppressed by expression of the INCENP mutant not binding to HP1.

Cells which stably express a wild type INCENP (WT), an INCENP mutant having a deletion of the HP1 binding region(ΔHP), or a 3A mutant obtained by substituting three amino acid residues PxVxI (HP1 binding site to INCENP) with alanine residues (3A, Non Patent Literature 6), were constructed. Using these cell lines, the effect of the binding of HP1 to INCENP on the activity of Aurora B was analyzed. In the cells expressing the INCENP mutants, the amount of HP1 coprecipitated with INCENP (myc, in FIG. 6B) is significantly low (FIG. 6B, central panel). In the analysis for kinase activity of Aurora B using GST-Hec1 as a substrate, Aurora B kinase activity is significantly suppressed, compared to the cells expressing the wild-type INCENP (FIG. 6B, right panel).

Figure 6C:
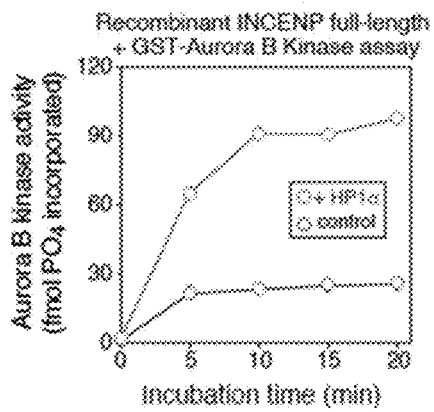
FIGS. 6C and 6D show Aurora B kinase activity in the presence or absence of HP1.
Figure 6D:
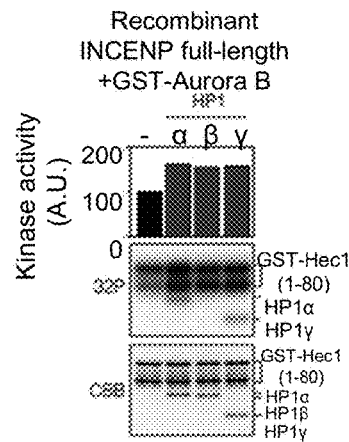
Figure 6E:
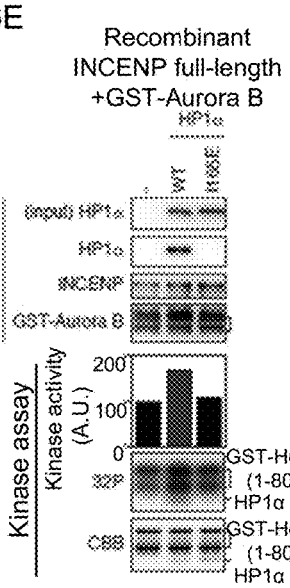
FIG. 6E shows that an HP1 mutant not binding to INCENP does not enhance the Aurora B kinase activity.

Using recombinant proteins of INCENP, Aurora B and HP1α, in vitro kinase assay was carried out (FIG. 6C). As a result, it was found that Aurora B exhibits high activity in the presence of HP1; however, the activity is significantly suppressed in the absence of HP1. It was found that not only HP1α but also HP1β and γ highly activate Aurora B (FIG. 6D). However, HP1 mutant I165E (Non Patent Literature 10), which cannot form a dimer, in other words, cannot bind to INCENP, does not activate Aurora B (FIG. 6E). Accordingly, it was shown that physical binding of HP1 to INCENP is required for activation of Aurora B, and that HP1 has an allosteric effect on Aurora B.

Figure 6F:
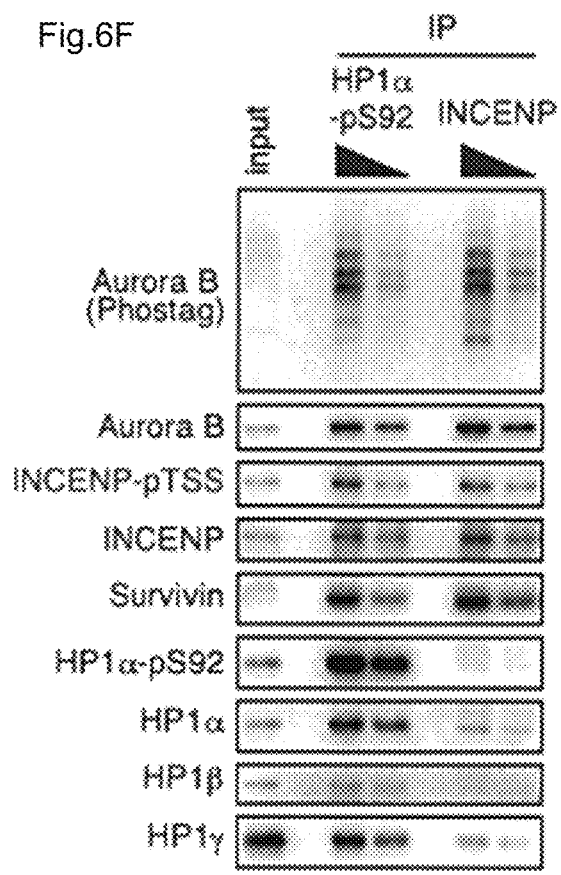
FIG. 6F shows analysis of phosphorylation of proteins constituting CPC to which phosphorylated HP1 is bound.

A faction of a protein binding to HP1 and a faction of a protein not binding to HP1 were subjected to analysis for examining the degree of phosphorylation of proteins constituting CPC (FIG. 6F). The phosphorylation of proteins was analyzed by Phostag-SDS-PAGE using 30 µM Phostag acrylamide (manufactured by NARD Institute) and 60 µM $MnCl_2$. It is known that the allosteric activation of Aurora B by INCENP is performed via phosphorylation. However, no difference was observed in phosphorylation of Aurora B and INCENP. From this, it is considered that the activity enhancement effect by HP1 is mediated by a mechanism different from conventional knowledge.

Figure 6G:
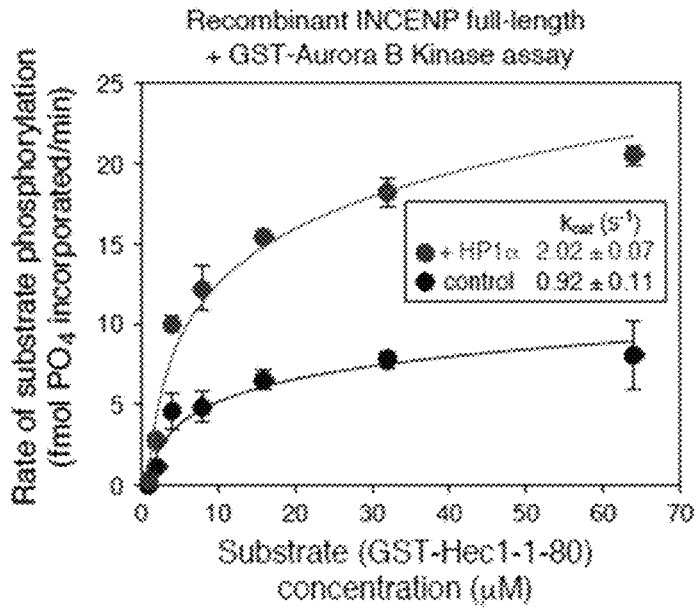
FIG. 6G shows that the rate of enzyme reaction of Aurora B increases by addition of HP1α.
Figure 6H:
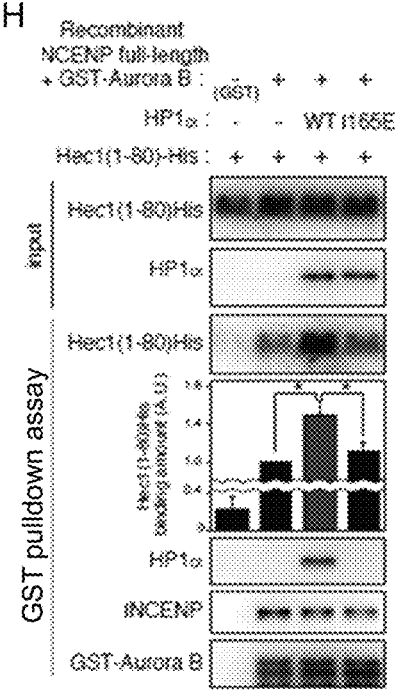
FIG. 6H shows that affinity of Aurora B to substrate is increased by binding of HP1 to INCENP.

Then, enzyme kinetics analysis of Aurora B was carried out. As a result (FIG. 6G), it was found that HP1α significantly increases the reaction rate of substrate phosphorylation by Aurora B per unit time. Further, analysis of proteins binding to GST-Aurora B was carried out by the GST pull down assay. As a result, the amount of Hec1 binding to GST-Aurora B increased in the conditions where HP1 can bind to INCENP. From this, it was found that the affinity of Aurora B to a substrate increases. As shown in FIG. 6H, the activity of Aurora B significantly decreases in the absence of HP1α or in the presence of HP1 mutant I165E which cannot bind to INCENP, compared to the presence of HP1α. Accordingly, binding of HP1α to INCENP is required for activating Aurora B.

The above results demonstrate that Aurora B is allosterically activated by binding of HP1 to CPC via INCENP, and that the activation of enzyme is conducted by reaction rate of the enzyme (i.e., basic function of the enzyme).

Figure 7A:
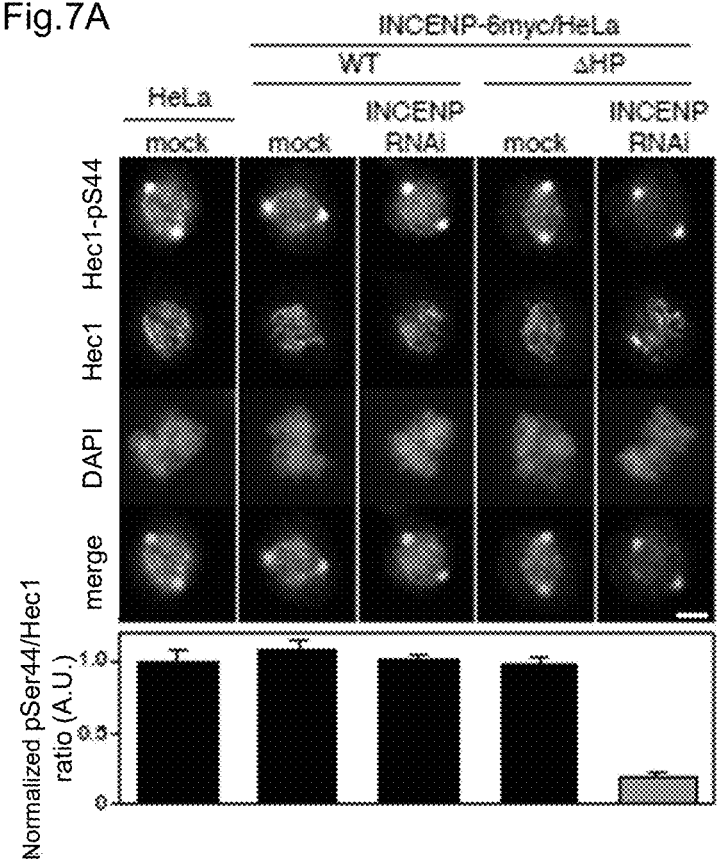
FIG. 7A shows that phosphorylation of Hec1 is suppressed in the INCENP mutant expressing cells not binding to HP1. Since the INCENP mutant (not binding to HP1) used in FIG. 7A having poor ability to activate Aurora B, the amount thereof localized in the centromere decreases. Then, in order to examine the effect of reduced CPC amount in the centromere, the same analysis was performed by CB-INCENP-EGFP, which forcibly localizes CPC in the centromere (FIG. 7B). As a result, phosphorylation of Hec1 was similarly suppressed. From this, it was found that allosteric activation by HP1 is primarily important.

To prove that HP1 allosterically regulates CPC within a cell, a change in phosphorylation of a substrate by Aurora B in the presence or absence of HP1 was analyzed. Phosphorylation of Hec1 serving as a substrate of Aurora B was analyzed by immunostaining with an anti-Hec1-pS44 antibody, using HeLa cells stably expressing a wild type INCENP (WT) or INCENP mutant having a deletion of the HP1 binding site (ΔHP mutant), while endogenous INCENP was depleted by RNAi. The relative fluorescence intensity, which was obtained by normalization to Hec1, was shown as a histogram. As shown in FIG. 7A, in the cells in which the ΔHP mutant was expressed and expression of endogenous INCENP was suppressed, the phosphorylation level of Hec1 was significantly low.

Figure 7B:
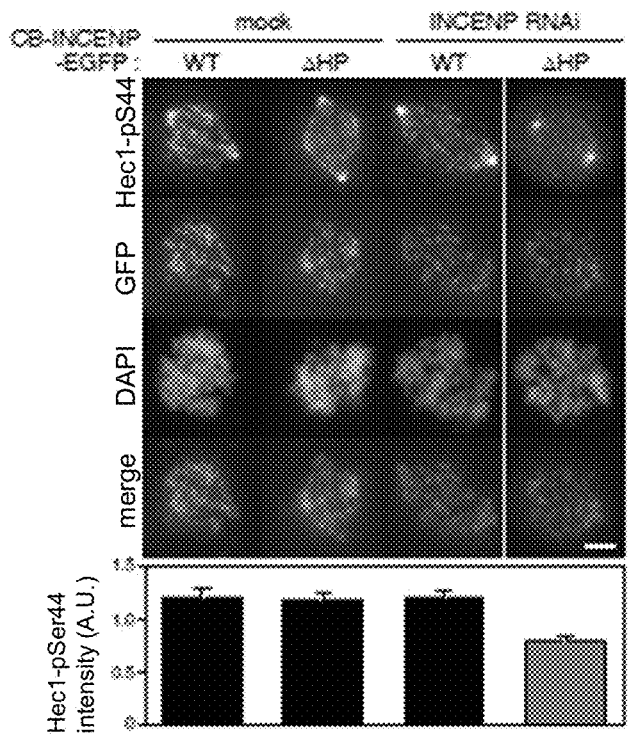
FIG. 7 The figures show that allosteric regulation of CPC by HP1 is required for phosphorylation of Aurora B substrate HEC1 in the centromere.

Further, whether the phosphorylation level is changed by HP1 was analyzed by expressing CB-INCENP-EGFP (fusion protein of INCENP, CENP-B, and EGFP) in place of endogenous INCENP, and localizing CPC in the centromere. It was shown that even though CPC is localized in the centromere, in the state where HP1 is not bound to CPC by ΔHP mutant, phosphorylation of a substrate mediated by Aurora B does not increase (FIG. 7B).

Figure 8A:
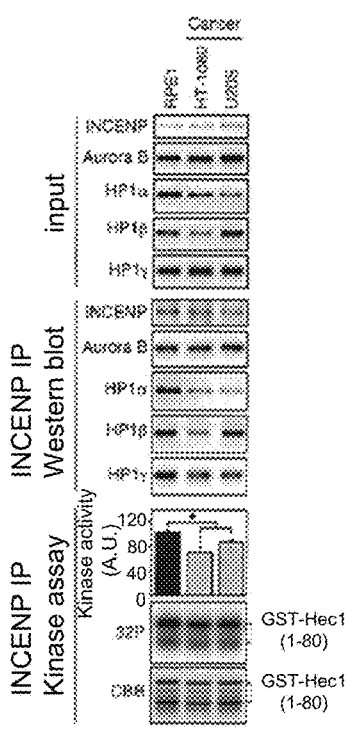
FIG. 8A shows difference in phosphorylation of substrate of Aurora B between non-transformed cell lines and cancer cell lines.

It was demonstrated that the binding of HP1 to CPC is required for activation of Aurora B. From this, it was considered that the activity of Aurora B in cancer cells may be lower than diploid cells. Using RPE1, HT-1080 and U2OS cells, immunoprecipitation by INCENP and in vitro kinase assay of Aurora B were carried out. In cancer cells, i.e., HT-1080 and U2OS cells, the amount of HP1 bound to CPC was low, and the activity of Aurora B was lower than non-transformed cells, RPE1 cells (FIG. 8A).

Figure 8B:
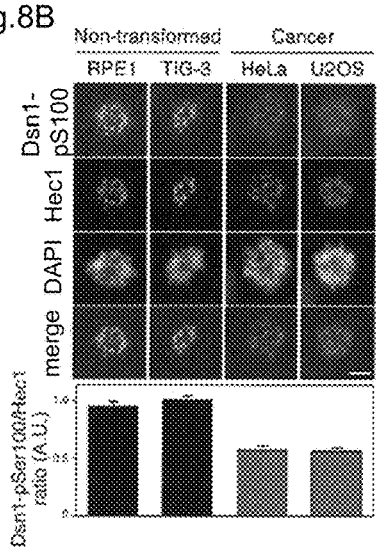
FIGS. 8B and C show difference in phosphorylation of Dsn1 (a substrate of Aurora B) between cell types.
Figure 8C:
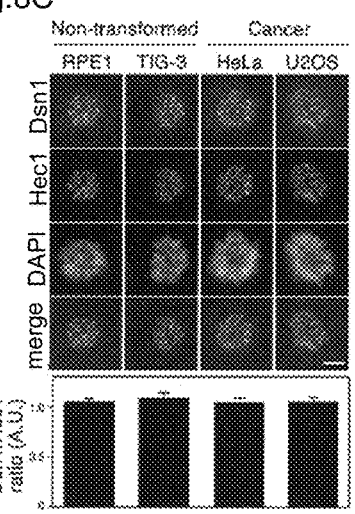
FIG. 8 The figures show difference in Aurora B activity between normal cell lines and cancer cell lines.
FIG. 8D shows a change in phosphorylation of substrate of Aurora B in RPE1 cells and HeLa cells by use of an INCENP mutant in the state where an endogenous INCENP was depleted.

Whether the difference in Aurora B activity between the cancer cells and diploid cells influences phosphorylation of a substrate of centromeres was analyzed by immunostaining of RPE1 and TIG-3 cells (non-transformed cells) and HeLa and U2OS cells (cancer cells). Phosphorylation of Dsn1, which is a substrate of Aurora B present in the centromere (FIG. 8B), and localization of Dsn1 (FIG. 8C) were analyzed by immunostaining. The relative fluorescence intensity was normalized to the fluorescence intensity of Hec1 and shown as a histogram. The amount of phosphorylated Dsn1 in the prometaphase of the mitosis in the cancer cells was significantly low, compared to that in the non-transformed cells.

Figure 8D:
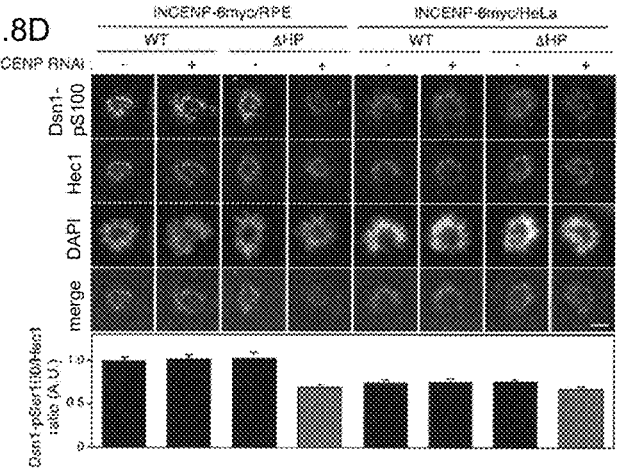

If the difference in phosphorylation mediated by Aurora B between the non-transformed cells and the cancer cells is due to the amount of HP1 bound to CPC, it was postulated that a big difference is seen in the non-transformed cells compared to cancer cells, in the conditions where binding of HP1 and INCENP is inhibited. In HeLa cells or RPE1 cells expressing wild type INCENP (WT) and mutant INCENP (ΔHP), while endogenous INCENP was depleted by RNAi, the amount of phosphorylated Dsn1 was analyzed by immunostaining (FIG. 8D). As a result, a big difference was observed in the RPE1 cells, in which ΔHP mutant was expressed, and expression of an endogenous INCENP was suppressed by RNAi, compared to the HeLa cells.

7. Effect of Binding of HP1 to CPC on Accurate Cell Division

Figure 9A:
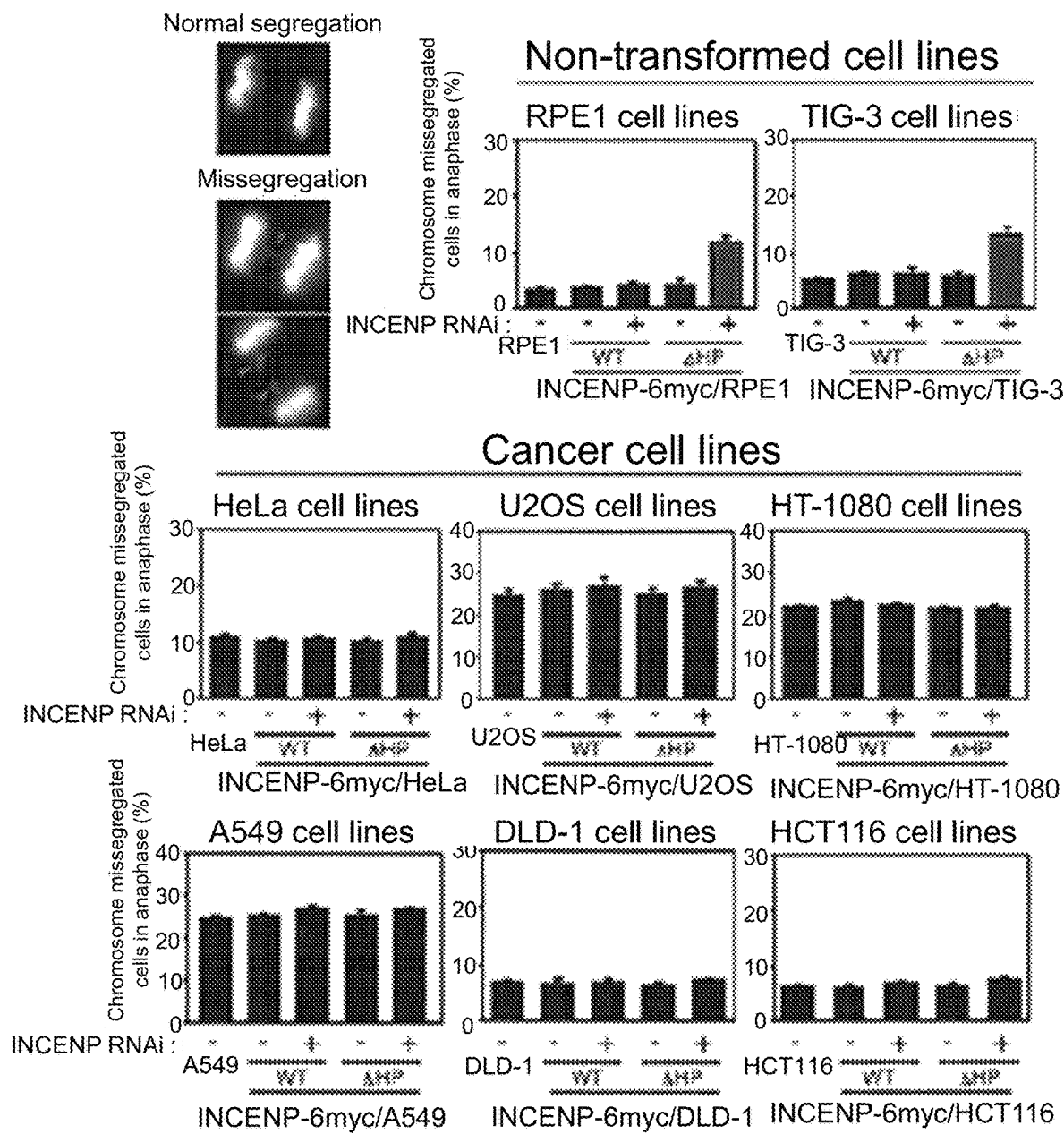
FIG. 9A shows a change in chromosome segregation error generated when cells express wild-type or mutant INCENP (not binding to HP1), in cell lines derived from normal cells or cancer cells.

Whether the binding of HP1 to CPC influences accurate cell division was analyzed (FIG. 9A). Wild type or ΔHP mutant was expressed in various types of cells, while endogenous INCENP was depleted by RNAi. In non-transformed cell lines; RPE1 and TIG-3 cell lines, when ΔHP mutant was expressed and endogenous INCENP was depleted, the number of chromosome segregation errors increased. In contrast, in cancer cell lines, the binding of HP1 to CPC does not influence stability of cell division. Since the amount of HP1 bound to CPC already decreased in the cancer cells, it seems that a further decrease will not give any influence.

Figure 9B:
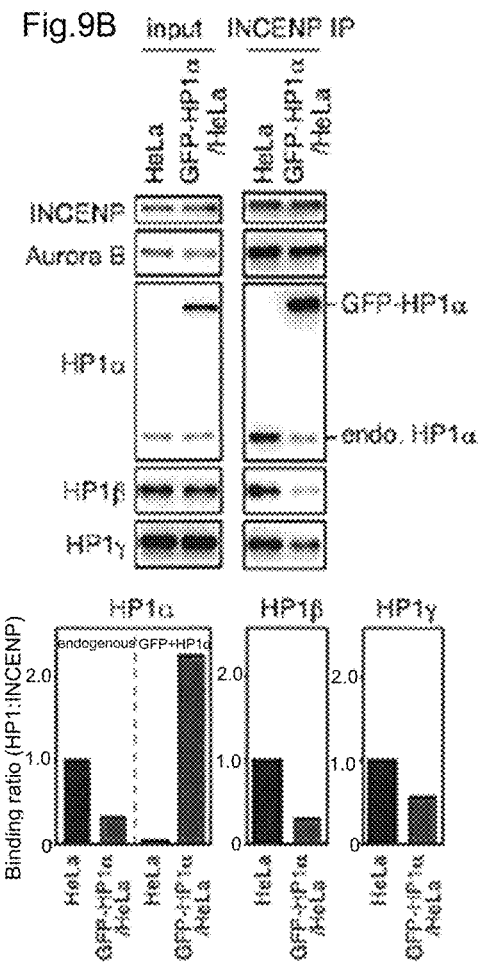
FIG. 9B shows analysis of chromosome segregation error by overexpressing HP1.
Figure 9C:
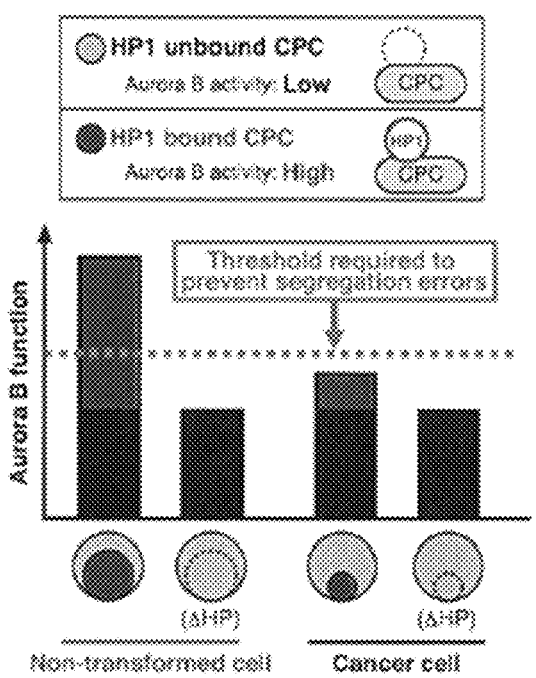
FIG. 9C schematically shows the binding of HP1 to CPC and Aurora B activity in normal cells and cancer cells. In cancer cells as compared with normal cells, the amount of HP1 necessary for accurate chromosome segregation is not bound to CPC. Consequently, kinase activity of Aurora B is insufficient, and the frequency of chromosome segregation errors increases.

The amount of HP1 bound to INCENP was analyzed in cells overexpressing HP1 (FIG. 9B). GFP-HP1α was excessively expressed in HeLa cells and immunoprecipitation with INCENP was carried out. Although HP1 excessively expressed was integrated into CPC, endogenous HP1 was dissociated in compensation. Because of this, even if HP1 expression level was enhanced, chromosomal segregation error was not suppressed. In cancer cells, unlike normal cells, HP1 is not bound to CPC in a sufficient amount required for accurate chromosome segregation. Because of this, it is considered that Aurora B kinase is not sufficiently activated and a frequency of chromosome separation errors increases (FIG. 9C).

Figure 9D:
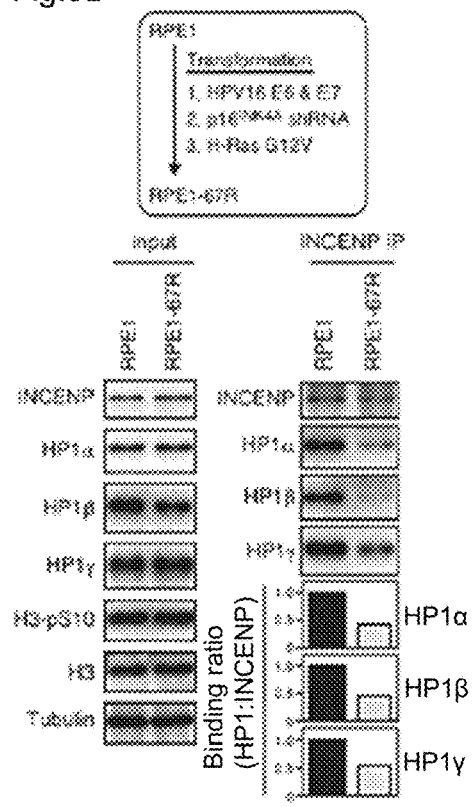
FIG. 9D shows that binding of HP1 to INCENP decreases by malignant transformation of RPE cells.

Further, binding to INCENP of RPE1-67R, which was obtained by transforming RPE1 cells, was analyzed by immunoprecipitation (FIG. 9D). As a result, it was observed that binding of HP1 to INCENP decreases by transformation of RPE1 cells; suggesting that transformation and binding of HP1 to INCENP have a strong correlation.

As described above, binding of HP1 to INCENP decreased in all cancer cells examined. It was also found that HP1 provide an allosteric effect by increasing the binding affinity of Aurora B to substrate, thereby maintaining and enhancing Aurora B activity.

8. Method for Screening for an Anticancer Agent

The above results show that in cancer cells the binding of INCENP and HP1 decreases and Aurora B does not appropriately function. Accordingly, a compound that influences chromosome instability can be obtained by screening for a compound influencing the interaction between HP1 and CPC via INCENP. It is considered that the compound further reducing the function of Aurora B in cancer cells acts so as to further increase chromosome instability of cancer cells. The compound could inhibit cell division of the cancer cells and induce cell death. An anticancer agent taking advantage of the improper function of Aurora B observed in cancer cells can be an anticancer agent with new-concept capable of targeting only cancer cells.

For screening for such a compound, a system allowing INCENP and HP1 to bind to each other in vitro is constructed and a compound that influences the binding may be screened. The compound that influences the binding of INCENP and HP1 can be screened by any method as long as it is known in the art. Particularly herein, systems using a binding assay and an alpha assay will be described.

Wild type HP1α and a region at positions 121 to 270 in INCENP (SEQ ID NO: 8, INCENP WT) were used in the binding assay. The region at positions 121 to 270 in INCENP contains an important motif PxVxI, required for binding to HP1. A mutant (SEQ ID NO: 9, INCENP 3A) was obtained by substituting three amino acids in this region with alanine residues and used as a control. A dissociation constant thereof was determined by isothermal titration calorimetry. As an isothermal titration calorimetry apparatus, any device may be used. For example, using MicroCal iTC2000 system (manufactured by GE healthcare biosciences), measurement may be carried out, in accordance with a conventional method.

The above peptides, to which His tag or GST tag was attached, were subjected to isothermal titration calorimetry to determine a dissociation constant. The results are shown in Table 1. Note that, the dissociation constant was computationally obtained based on average values of 5 experiments. INCENP WT binds to HP1α with high affinity of dissociation constant 0.102 μM. It shows that extremely sensitive system for detecting the binding of INCENP and HP1 was constructed. Since INCENP 3A mutant obtained by introducing a mutation in the binding motif to HP1 does not bind to HP1, the above binding means a specific binding.

TABLE 1

|  | Binding | Kd (μM) |
| --- | --- | --- |
| INCENP WT | O | 0.102 |
| INCENP 3A | X | — |

If a candidate compound is added in the binding assay system, a compound influencing the binding of INCENP and HP1 can be screened. Further, a system for analyzing the binding of HP1 and INCENP based on an alpha assay, which is more sensitive and easier in operation, was constructed. The interaction between HP1α and INCENP was determined by using acceptor beads or donor beads that can capture His tag or GST tag and detecting fluorescent signal in accordance with a conventional method. As a result of that His tag or GST tag was attached to HP1α and a region at positions 160 to 210 in INCENP (SEQ ID NO: 10) and the aforementioned alpha assay using acceptor beads and donor beads was carried out, a binding can be sensitively detected. Accordingly, owing to HTS using the binding assay or alpha assay, compounds influencing the binding of HP1 and INCENP can be screened.

As described above, candidate compounds influencing the binding of INCENP and HP1 are selected by HTS using an in vitro analysis (as a first step); and the chromosome segregation accuracy is evaluated based on observation of cell division by, e.g. live-imaging (as a second step). In this manner, candidate compounds are further narrowed to select a compound satisfying the concept of the present invention. Whether or not a compound specifically acts on cancer cells can be evaluated by analyzing chromosome segregation by live-imaging.

In addition, an antibody for specifically detecting phosphorylation of serine at position 92 of HP1 directly detects phosphorylation of HP1; besides, specifically reflects the function of Aurora B. Thus, the antibody is highly valuable not only as a screening tool of the present invention but also as a research tool.

The invention claimed is:

1. A method for evaluating chromosome instability to screen for an anticancer agent, comprising:
   selecting a compound as an anticancer agent candidate and adding the selected compound to a system comprising heterochromatin protein 1 (HP1) and inner centromere protein (INCENP), wherein the HP1 and the INCENP are allowed to bind to each other;
   determining a change of interaction or binding of HP1α to the INCENP in the system with the selected compound added; and
   evaluating chromosome instability based on the determined change of interaction or binding of the HP1α to the INCENP, wherein if the determined change of interaction or binding is decreased, the chromosome instability is evaluated as being increased, to screen the selected compound as the anticancer agent;
   wherein the system is one of a binding assay system or an alpha assay system.

2. The method for evaluating chromosome instability according to claim 1, wherein
   determining the change of interaction or binding of HP1α to INCENP includes analyzing phosphorylation of HP1a to determine binding of HP1α to CPC (chromosomal passenger complex) and Aurora B activity, wherein the phosphorylation of HP1α is phosphorylation of serine at position 92 of HP1α.

3. The method for evaluating chromosome instability to screen for an anticancer agent according to claim 1, further comprising:
   measuring accuracy of chromosome segregation with the selected compound during cell division by imaging analysis.

* * * * *